(12) United States Patent
Wood et al.

(10) Patent No.: US 7,722,565 B2
(45) Date of Patent: May 25, 2010

(54) ACCESS SYSTEM

(75) Inventors: Bradford Johns Wood, Potomac, MD (US); Neil David Glossop, Toronto (CA)

(73) Assignees: Traxtal, Inc., Toronto, Ontario (CA); The United States of America as represented by the Department of Health and Human Services, Washington, DC (US)

( * ) Notice: Subject to any disclaimer, the term of this patent is extended or adjusted under 35 U.S.C. 154(b) by 119 days.

(21) Appl. No.: 11/718,679

(22) PCT Filed: Nov. 4, 2005

(86) PCT No.: PCT/US2005/039772
§ 371 (c)(1),
(2), (4) Date: Sep. 11, 2007

(87) PCT Pub. No.: WO2006/057786
PCT Pub. Date: Jun. 1, 2006

(65) Prior Publication Data
US 2008/0071215 A1    Mar. 20, 2008

Related U.S. Application Data

(60) Provisional application No. 60/625,186, filed on Nov. 5, 2004.

(51) Int. Cl.
*A61M 5/00* (2006.01)
(52) U.S. Cl. ........................................ 604/116; 604/117
(58) Field of Classification Search .................. 604/116, 604/117, 174–180; 606/130, 96–98
See application file for complete search history.

(56) References Cited

U.S. PATENT DOCUMENTS

| 3,021,842 A | 2/1962 | Flood |
| 4,080,706 A | 3/1978 | Heilman et al. ............... 29/173 |

(Continued)

FOREIGN PATENT DOCUMENTS

AU      6367896      2/1997

(Continued)

OTHER PUBLICATIONS

International Search Report Apr. 25, 2006.

(Continued)

*Primary Examiner*—Nicholas D Lucchesi
*Assistant Examiner*—Gerald Landry, II

(57) ABSTRACT

The invention provides systems and methods for providing access to a target site. Example systems may include a needle, a grid to guide the needle, a plate with an aperture, a member coupled to the plate and including a semispherical surface, and a hub slideably coupled to the plate by a guide. The system may also include a needle coupled to the hub, the needle including a magnetically trackable sensor positioned in a tip of the needle. The semispherical surface can be positioned against skin of a body and the hub slid relative to the plate along the guide to insert the needle through the aperture in the plate into the body until the tip reaches a target site. The hub can be locked by a lock mechanism when the tip of the needle reaches the target site, and an action performed on the target site through the needle.

23 Claims, 19 Drawing Sheets

U.S. PATENT DOCUMENTS

| | | | | |
|---|---|---|---|---|
| 4,279,252 A | 7/1981 | Martin | 128/349 R |
| 4,697,595 A | 10/1987 | Breyer et al. | 128/660 |
| 4,722,056 A | 1/1988 | Roberts et al. | 364/413 |
| 4,777,951 A | 10/1988 | Cribier et al. | 128/344 |
| 4,887,606 A | 12/1989 | Yock et al. | 128/662.05 |
| 4,895,168 A | 1/1990 | Machek | 128/772 |
| 4,935,019 A | 6/1990 | Papp, Jr. | 604/362 |
| 4,961,433 A | 10/1990 | Christian | 128/772 |
| 5,014,708 A | 5/1991 | Hayashi et al. | 128/653 R |
| 5,042,486 A | 8/1991 | Pfeiler et al. | 128/653 R |
| 5,045,080 A | 9/1991 | Dyer et al. | 604/362 |
| 5,085,659 A | 2/1992 | Rydell | 606/47 |
| 5,116,345 A * | 5/1992 | Jewell et al. | 606/130 |
| 5,187,658 A | 2/1993 | Cline et al. | 364/413.13 |
| 5,204,625 A | 4/1993 | Cline et al. | 324/306 |
| 5,207,675 A | 5/1993 | Canady | 606/40 |
| 5,211,165 A | 5/1993 | Dumoulin et al. | 128/653.1 |
| 5,221,283 A | 6/1993 | Chang | 606/130 |
| 5,247,935 A | 9/1993 | Cline et al. | 128/653.2 |
| 5,251,127 A | 10/1993 | Raab | 364/413.13 |
| 5,251,635 A | 10/1993 | Dumoulin et al. | 128/653.2 |
| 5,255,680 A | 10/1993 | Darrow et al. | 128/653.1 |
| 5,265,610 A | 11/1993 | Darrow et al. | 128/653.1 |
| 5,271,400 A | 12/1993 | Dumoulin et al. | 128/653.2 |
| 5,275,165 A | 1/1994 | Ettinger et al. | 128/653.2 |
| 5,290,266 A | 3/1994 | Rohling et al. | 604/272 |
| 5,291,010 A | 3/1994 | Tsuji | 250/208.1 |
| 5,291,890 A | 3/1994 | Cline et al. | 128/653.2 |
| 5,304,933 A | 4/1994 | Vavrek et al. | 324/318 |
| 5,305,203 A | 4/1994 | Raab | 364/413.13 |
| 5,307,812 A | 5/1994 | Hardy et al. | 128/653.2 |
| 5,318,025 A | 6/1994 | Dumoulin et al. | 128/653.2 |
| 5,323,779 A | 6/1994 | Hardy et al. | 128/653.2 |
| 5,327,884 A | 7/1994 | Hardy et al. | 128/653.2 |
| 5,353,808 A | 10/1994 | Viera | 128/772 |
| 5,365,927 A | 11/1994 | Roemer et al. | 128/653.2 |
| 5,368,031 A | 11/1994 | Cline et al. | 128/653.2 |
| 5,368,032 A | 11/1994 | Cline et al. | 128/653.2 |
| 5,377,678 A | 1/1995 | Dumoulin et al. | 128/653.1 |
| 5,383,454 A | 1/1995 | Bucholz | 128/653.1 |
| 5,383,465 A | 1/1995 | Lesny et al. | 128/662.05 |
| 5,386,828 A | 2/1995 | Owens et al. | 128/653.1 |
| 5,389,101 A | 2/1995 | Heilbrun et al. | 606/130 |
| 5,391,199 A | 2/1995 | Ben-Haim | 607/122 |
| 5,396,905 A | 3/1995 | Newman et al. | 128/849 |
| 5,400,383 A | 3/1995 | Yassa et al. | 378/98.2 |
| 5,437,277 A | 8/1995 | Dumoulin et al. | 128/653.1 |
| 5,443,066 A | 8/1995 | Dumoulin et al. | 128/653.1 |
| 5,443,068 A | 8/1995 | Cline et al. | 128/653.5 |
| 5,445,150 A | 8/1995 | Dumoulin et al. | 128/653.1 |
| 5,465,732 A | 11/1995 | Abele | 128/772 |
| 5,480,382 A | 1/1996 | Hammerslag et al. | 604/95 |
| 5,490,840 A | 2/1996 | Uzgiris et al. | 604/22 |
| 5,493,598 A | 2/1996 | Yassa et al. | 378/98.2 |
| 5,526,812 A | 6/1996 | Dumoulin et al. | 128/653.1 |
| 5,526,814 A | 6/1996 | Cline et al. | 128/653.2 |
| 5,558,091 A | 9/1996 | Acker et al. | 128/653.1 |
| 5,603,318 A | 2/1997 | Heilbrun et al. | 128/630 |
| 5,645,065 A | 7/1997 | Shapiro et al. | 128/653.1 |
| 5,646,524 A | 7/1997 | Gilboa | 324/207.17 |
| 5,646,525 A | 7/1997 | Gilboa | 324/207.17 |
| 5,647,373 A | 7/1997 | Paltieli | 128/749 |
| 5,705,014 A | 1/1998 | Schenck et al. | 156/272.4 |
| 5,713,858 A | 2/1998 | Heruth et al. | 604/93 |
| 5,715,166 A | 2/1998 | Besl et al. | 364/474.24 |
| 5,715,822 A | 2/1998 | Watkins et al. | 128/653.5 |
| 5,740,802 A | 4/1998 | Nafis et al. | 128/653.1 |
| 5,749,835 A | 5/1998 | Glantz | 600/424 |
| 5,769,790 A | 6/1998 | Watkins et al. | 600/439 |
| 5,769,861 A | 6/1998 | Vilsmeier | 606/130 |
| 5,848,969 A | 12/1998 | Panescu et al. | 600/462 |
| 5,857,032 A | 1/1999 | Wang et al. | 382/154 |
| 5,868,673 A | 2/1999 | Vesely | 600/407 |
| 5,871,487 A * | 2/1999 | Warner et al. | 606/130 |
| 5,873,845 A | 2/1999 | Cline et al. | 601/3 |
| 5,880,976 A | 3/1999 | DiGioia, III et al. | 364/578 |
| 5,931,786 A | 8/1999 | Whitmore, III et al. | 600/459 |
| 5,944,023 A | 8/1999 | Johnson et al. | 128/899 |
| 5,978,696 A | 11/1999 | VomLehn et al. | 600/411 |
| 6,016,439 A | 1/2000 | Acker | 600/411 |
| 6,036,682 A | 3/2000 | Lange et al. | 604/529 |
| 6,073,043 A | 6/2000 | Schneider | 600/424 |
| 6,097,978 A | 8/2000 | Demarais et al. | 600/429 |
| 6,106,476 A | 8/2000 | Corl et al. | 600/486 |
| 6,141,576 A | 10/2000 | Littmann et al. | 600/381 |
| 6,147,480 A | 11/2000 | Osadchy et al. | 324/67 |
| 6,165,184 A | 12/2000 | Verdura et al. | 606/148 |
| 6,188,355 B1 | 2/2001 | Gilboa | 342/448 |
| 6,196,980 B1 | 3/2001 | Akerfeldt et al. | 600/585 |
| 6,203,493 B1 | 3/2001 | Ben-Haim | 600/117 |
| 6,203,543 B1 | 3/2001 | Glossop | 606/60 |
| 6,205,411 B1 | 3/2001 | DiGioia, III et al. | 703/11 |
| 6,210,339 B1 | 4/2001 | Kiepen et al. | 600/486 |
| 6,216,029 B1 | 4/2001 | Paltieli | 600/407 |
| 6,226,543 B1 | 5/2001 | Gilboa et al. | 600/407 |
| 6,233,476 B1 | 5/2001 | Strommer et al. | 600/424 |
| 6,235,038 B1 | 5/2001 | Hunter et al. | 606/130 |
| 6,241,690 B1 | 6/2001 | Burkett et al. | 600/585 |
| 6,266,551 B1 | 7/2001 | Osadchy et al. | 600/424 |
| 6,266,552 B1 | 7/2001 | Slettenmark | 600/424 |
| 6,272,370 B1 | 8/2001 | Gillies et al. | 600/411 |
| 6,272,371 B1 | 8/2001 | Shlomo | 600/424 |
| 6,285,898 B1 | 9/2001 | Ben-Haim | 600/374 |
| 6,285,903 B1 | 9/2001 | Rosenthal et al. | 600/433 |
| 6,288,785 B1 | 9/2001 | Frantz et al. | 356/614 |
| 6,308,089 B1 | 10/2001 | von der Ruhr et al. | 600/338 |
| 6,314,310 B1 | 11/2001 | Ben-Haim et al. | 600/424 |
| 6,317,621 B1 | 11/2001 | Graumann et al. | 600/424 |
| 6,332,089 B1 | 12/2001 | Acker et al. | 600/424 |
| 6,336,906 B1 | 1/2002 | Hammarstrom et al. | 600/585 |
| 6,338,716 B1 | 1/2002 | Hossack et al. | 600/459 |
| 6,356,783 B1 | 3/2002 | Hubbard, Jr. | 600/546 |
| 6,380,732 B1 | 4/2002 | Gilboa | 324/207.17 |
| 6,381,485 B1 | 4/2002 | Hunter et al. | 600/407 |
| 6,383,174 B1 | 5/2002 | Eder | 606/1 |
| 6,385,482 B1 | 5/2002 | Boksberger et al. | 600/424 |
| 6,427,079 B1 | 7/2002 | Schneider et al. | 600/424 |
| 6,442,417 B1 | 8/2002 | Shahidi et al. | 600/429 |
| 6,468,265 B1 | 10/2002 | Evans et al. | 606/1 |
| 6,473,635 B1 | 10/2002 | Rasche | 600/428 |
| 6,484,118 B1 | 11/2002 | Govari | 702/150 |
| 6,493,589 B1 | 12/2002 | Medhkour et al. | 607/99 |
| 6,498,944 B1 | 12/2002 | Ben-Haim et al. | 600/407 |
| 6,499,488 B1 | 12/2002 | Hunter et al. | 128/899 |
| 6,500,114 B1 | 12/2002 | Petitto et al. | 600/156 |
| 6,512,958 B1 | 1/2003 | Swoyer et al. | 607/117 |
| 6,529,758 B2 | 3/2003 | Shahidi | 600/407 |
| 6,547,782 B1 | 4/2003 | Taylor | 606/14 |
| 6,558,333 B2 | 5/2003 | Gilboa et al. | 600/466 |
| 6,574,492 B1 | 6/2003 | Ben-Haim et al. | 600/374 |
| 6,574,498 B1 | 6/2003 | Gilboa | 600/424 |
| 6,580,938 B1 | 6/2003 | Acker | 600/424 |
| 6,585,654 B2 | 7/2003 | White et al. | 600/463 |
| 6,588,333 B1 | 7/2003 | Homer et al. | 101/32 |
| 6,591,127 B1 | 7/2003 | McKinnon | 600/411 |
| 6,591,129 B1 | 7/2003 | Ben-Haim et al. | 600/424 |
| 6,592,573 B2 * | 7/2003 | Castaneda et al. | 606/1 |
| 6,593,884 B1 | 7/2003 | Gilboa et al. | 342/448 |
| 6,615,155 B2 | 9/2003 | Gilboa | 702/150 |
| 6,619,838 B2 | 9/2003 | Bencini et al. | 378/190 |
| 6,628,987 B1 | 9/2003 | Hill et al. | 607/9 |
| 6,690,963 B2 | 2/2004 | Ben-Haim et al. | 600/424 |
| 6,702,780 B1 | 3/2004 | Gilboa et al. | 604/95.04 |
| 6,711,429 B1 | 3/2004 | Gilboa et al. | 600/407 |

| | | | |
|---|---|---|---|
| 6,719,700 B1 | 4/2004 | Willis | 600/462 |
| 6,735,471 B2 | 5/2004 | Hill et al. | 607/2 |
| 6,748,112 B1 | 6/2004 | Nguyen et al. | 382/203 |
| 6,753,873 B2 | 6/2004 | Dixon et al. | 345/542 |
| 6,782,287 B2 | 8/2004 | Grzeszczuk et al. | 600/424 |
| 6,783,536 B2 | 8/2004 | Vilsmeier et al. | 606/130 |
| 6,785,571 B2 | 8/2004 | Glossop | 600/424 |
| 6,788,967 B2 | 9/2004 | Ben-Haim et al. | 600/424 |
| 6,792,303 B2 | 9/2004 | Taimisto | 600/424 |
| 6,893,429 B2 | 5/2005 | Petersen | 604/537 |
| 6,895,268 B1 | 5/2005 | Rahn et al. | 600/429 |
| 6,916,290 B2 | 7/2005 | Hedengren et al. | 600/549 |
| 7,085,400 B1 | 8/2006 | Holsing et al. | 382/103 |
| 7,386,339 B2 | 6/2008 | Strommer et al. | 600/424 |
| 7,570,791 B2 | 8/2009 | Frank et al. | 382/132 |
| 2001/0008972 A1 | 7/2001 | Gielen | 607/45 |
| 2001/0011175 A1 | 8/2001 | Hunter et al. | 606/130 |
| 2001/0031919 A1 | 10/2001 | Strommer et al. | 600/424 |
| 2001/0031985 A1 | 10/2001 | Gilboa et al. | 607/1 |
| 2001/0036245 A1 | 11/2001 | Kienzle, III et al. | 378/4 |
| 2001/0038354 A1 | 11/2001 | Gilboa | 342/450 |
| 2001/0039419 A1 | 11/2001 | Francischelli et al. | 606/42 |
| 2001/0047133 A1 | 11/2001 | Gilboa et al. | 600/429 |
| 2002/0005719 A1 | 1/2002 | Gilboa et al. | 324/309 |
| 2002/0038102 A1 | 3/2002 | McFarlin et al. | 604/30 |
| 2002/0042571 A1 | 4/2002 | Gilboa et al. | 600/429 |
| 2002/0049375 A1 | 4/2002 | Strommer et al. | 600/407 |
| 2002/0049451 A1* | 4/2002 | Parmer et al. | 606/108 |
| 2002/0062203 A1 | 5/2002 | Gilboa | 702/150 |
| 2002/0074005 A1* | 6/2002 | Hogg et al. | 128/899 |
| 2002/0087101 A1 | 7/2002 | Barrick et al. | 600/587 |
| 2002/0143317 A1* | 10/2002 | Glossop | 604/529 |
| 2002/0156363 A1 | 10/2002 | Hunter et al. | 600/410 |
| 2002/0156417 A1 | 10/2002 | Rich et al. | 604/65 |
| 2002/0165448 A1 | 11/2002 | Ben-Haim et al. | 600/424 |
| 2002/0165468 A1 | 11/2002 | Tolkowsky et al. | 600/587 |
| 2003/0018251 A1 | 1/2003 | Solomon | 600/427 |
| 2003/0021455 A1 | 1/2003 | Dixon et al. | 382/132 |
| 2003/0028233 A1 | 2/2003 | Vardi et al. | 623/1.11 |
| 2003/0030004 A1 | 2/2003 | Dixon et al. | 250/370.09 |
| 2003/0074011 A1 | 4/2003 | Gilboa et al. | 606/130 |
| 2003/0092988 A1 | 5/2003 | Makin | 600/439 |
| 2003/0114778 A1 | 6/2003 | Vilsmeier et al. | 600/585 |
| 2003/0114846 A1 | 6/2003 | Fuimaono et al. | 606/41 |
| 2003/0130576 A1 | 7/2003 | Seeley et al. | 600/426 |
| 2003/0171680 A1* | 9/2003 | Paltieli | 600/459 |
| 2003/0171739 A1 | 9/2003 | Murphy et al. | 606/1 |
| 2003/0208102 A1 | 11/2003 | Gilboa | 600/41 |
| 2003/0208296 A1 | 11/2003 | Brisson et al. | 700/117 |
| 2003/0216639 A1 | 11/2003 | Gilboa et al. | 600/424 |
| 2003/0220557 A1 | 11/2003 | Cleary et al. | 600/409 |
| 2004/0019274 A1 | 1/2004 | Galloway, Jr. et al. | 600/425 |
| 2004/0024309 A1 | 2/2004 | Ferre et al. | 600/424 |
| 2004/0034297 A1 | 2/2004 | Darrow et al. | 600/407 |
| 2004/0034300 A1 | 2/2004 | Verard et al. | 600/424 |
| 2004/0036867 A1 | 2/2004 | Jedamzik et al. | 356/243.1 |
| 2004/0077942 A1 | 4/2004 | Hall et al. | 600/428 |
| 2004/0078036 A1 | 4/2004 | Keidar | 606/41 |
| 2004/0097804 A1 | 5/2004 | Sobe | 600/424 |
| 2004/0097805 A1 | 5/2004 | Verard et al. | 600/428 |
| 2004/0097806 A1 | 5/2004 | Hunter et al. | 600/434 |
| 2004/0138548 A1 | 7/2004 | Strommer et al. | 600/407 |
| 2004/0143188 A1 | 7/2004 | Barzell et al. | 600/439 |
| 2004/0147837 A1 | 7/2004 | Macaulay et al. | 600/424 |
| 2004/0147939 A1 | 7/2004 | Rabkin et al. | 606/108 |
| 2004/0158146 A1 | 8/2004 | Mate et al. | 600/427 |
| 2004/0221853 A1 | 11/2004 | Miller | 128/207.14 |
| 2004/0234933 A1 | 11/2004 | Dawson et al. | 434/262 |
| 2004/0249267 A1 | 12/2004 | Gilboa | 600/424 |
| 2004/0254458 A1 | 12/2004 | Govari | 600/437 |
| 2005/0033149 A1 | 2/2005 | Strommer et al. | 600/407 |
| 2005/0038337 A1 | 2/2005 | Edwards | 600/424 |
| 2005/0049520 A1 | 3/2005 | Nakao | 600/562 |
| 2005/0054900 A1 | 3/2005 | Mawn et al. | 600/156 |
| 2005/0059886 A1 | 3/2005 | Webber | 600/426 |
| 2005/0085715 A1 | 4/2005 | Dukesherer et al. | 600/424 |
| 2005/0085720 A1 | 4/2005 | Jascob et al. | 600/424 |
| 2005/0085793 A1 | 4/2005 | Glossop | 604/529 |
| 2005/0107688 A1 | 5/2005 | Strommer | 600/424 |
| 2005/0182295 A1 | 8/2005 | Soper et al. | 600/117 |
| 2005/0182319 A1 | 8/2005 | Glossop | 600/424 |
| 2005/0228270 A1 | 10/2005 | Lloyd et al. | 600/424 |
| 2006/0147100 A1 | 7/2006 | Fitzpatrick | 382/131 |
| 2007/0032862 A1 | 2/2007 | Weber et al. | 623/1.34 |

FOREIGN PATENT DOCUMENTS

| | | |
|---|---|---|
| AU | 722539 | 8/2000 |
| BR | 9609484 | 12/1999 |
| CA | 2226938 | 2/1997 |
| DE | 69420228 D | 9/1999 |
| DE | 69420228 T | 4/2000 |
| DE | 19845267 C1 | 5/2000 |
| EP | 0 845 959 | 6/1998 |
| EP | 0 654 244 | 8/1999 |
| EP | 1 466 552 | 10/2004 |
| IL | 0107523 | 1/2000 |
| IL | 0114610 | 7/2000 |
| JP | 10-277047 | 10/1998 |
| JP | 2000500031 T | 1/2000 |
| JP | 2005152463 | 6/2005 |
| WO | WO 97/03609 | 2/1997 |
| WO | WO 98/56295 A | 12/1998 |
| WO | WO 00/22904 | 4/2000 |

OTHER PUBLICATIONS

Tanase, Dafina, et al., "Magnetic Sensors for Use on Guide Wires or Catheters", in *SeSens* 2001, in press 2002, pp. 868-872.

Solomon, Stephen B., et al., "Three-Dimensional CT-Guided Bronchoscopy with a Real-Time Electromagnetic Position Sensor: A Comparison of Two Image Registration Methods", *Chest*, vol. 118, No. 6, Dec. 2000, pp. 1783-1787.

Solomon, Stephen B., et al., "Real-Time Cardiac Catheter Navigation on Three-Dimensional CT Images", *Journal of Interventional Cardiac Electrophysiology*, vol. 8, 2003, pp. 27-36.

Palti-Wasserman, Daphna, et al., "Identifying and Tracking a Guide Wire in the Coronary Arteries During Angioplasty from X-Ray Images", *IEEE Transactions on Biomedical Engineering*, vol. 44, No. 2, Feb. 1997, pp. 152-164.

Baert, Shirley A. M., et al., "Endpoint Localization in Guide Wire Tracking During Endovascular Interventions", *Academic Radiology*, vol. 10, No. 12, Dec. 2003, pp. 1424-1432.

Baert, Shirley A. M., et al., "Three-Dimensional Guide-Wire Reconstruction from Biplane Image Sequences for Integrated Display in 3-D Vasculature", *IEEE Transactions on Medical Imaging*, vol. 22, No. 10, Oct. 2003, pp. 1252-1258.

Baert, Shirley A. M., et al., "Guide-Wire Tracking During Endovascular Interventions", *IEEE Transactions on Medical Imaging*, vol. 22, No. 8, Aug. 2003, pp. 965-972.

Kobashi, Keiji, et al., "A New Biomechanical Model Based Approach on Brain Shift Compensation", *MICCAI 2003*, LNCS 2878, 2003, pp. 59-66.

Timinger, Holger, et al., "Motion Compensation for Interventional Navigation on 3D Static Roadmaps Based on an Affine Model and Gating", *Physics in Medicine and Biology*, vol. 49, 2004, pp. 719-732.

Lorigo, Liana M., et al., "Curves: Curve Evolution for Vessel Segmentation", *Medical Image Analysis*, vol. 5, 2001, pp. 195-206 (pp. 1-14).

Chassat, Fabrice, et al., "Experimental Protocol of Accuracy Evaluation of 6-D Localizers for Computer-Integrated Surgery: Application to Four Optical Localizers", *MICCAI 98*, vol. 1496, Oct. 1998, Cambridge, Massachusetts U.S.A., p. 277-284.

Tsai, Roger Y., "A Versatile Camera Calibration Technique for High-Accuracy 3D Machine Vision Metrology Using Off-the-Shelf TV Cameras and Lenses", *IEEE Journal of Robotics and Automation*, vol. RA-3, No. 4, Aug. 1987, pp. 323-344.

"Semi-Automatic Registration for Image Guided Surgery", Traxtal poster presented at CAOS '99 (Computer Assisted Orthopaedic Surgery, 4th International Symposium), MICCAI, Mar. 17-19, 1999, Davos, Switzerland, 1 page.

Wu, Xiaohui, et al., "A Direction Space Interpolation Technique for Calibration of Electromagnetic Surgical Navigation Systems", Lecture Notes in Computer Science Medical Image Computing and Computer-Assisted Intervention, *MICCAI 2003*, LNCS 2879, Publisher: Springer-Verlag Heidelberg, 2003, pp. 215-222.

Livyatan, Harel, "Calibration and Gradient-Based Rigid Registration of Fluoroscopic X-rays to CT, for Intra Operative Navigation", Master of Science Thesis, supervised by Prof. Leo Joskowicz, School of Computer Science and Engineering, The Hebrew University of Jerusalem, Israel, Jul. 27, 2003, 92 pages.

SuperDimension, Ltd, web page, updated in Sep. 2005, 1 page.

Schweikard, Achim, et al., "Robotic Motion Compensation for Respiratory Movement During Radiosurgery", *Computer Aided Surgery*, vol. 5, 2000, pp. 263-277.

Solomon, Stephen B., et al., "Real-Time Bronchoscope Tip Localization Enables Three-Dimensional CT Image Guidance for Transbronchial Needle Aspiration in Swine", *Chest*, vol. 114, No. 5, Nov. 1998, pp. 1405-1410.

Ellsmere, James, et al., "A Navigation System for Augmenting Laparoscopic Ultrasound", Center for Integration of Medicine and Innovative Technology, Cambridge, Massachusetts, 8 pages.

Hofstetter, R., et al., "Fluoroscopy Based Surgical Navigation—Concept and Clinical Applications", Maurice E. Muller Institute for Biomechanics, University of Bern, Switzerland, 1997, 3 pages.

Tapper, Michael, et al., "Problems Encountered in the Implementation of Tsai's Algorithm for Camera Calibration", *Proc. 2002 Australasian Conference on Robotics and Automation*, Auckland, Nov. 27-29, 2002, pp. 66-70.

Summers, Ronald M., et al., "Colonic Polyps: Complementary Role of Computer-Aided Detection in CT Colonography", *Radiology*, vol. 225, No. 2, Nov. 2002, pp. 391-399.

Hara, A. K., et al., "Reducing Data Size and Radiation Dose for CT Colonography", *AJR*, vol. 168, May 1997, pp. 1181-1184.

Knaan, Dotan, et al., Effective Intensity-Based 2D/3D Rigid Registration Between Fluoroscopic X-Ray and CT, *MICCAI*, vol. 1, 2003, pp. 351-358.

Gee, A. H., et al., "3D Ultrasound Probe Calibration Without a Position Sensor", CUED/F-INFENG/TR 488, University of Cambridge, Department of Engineering, Sep. 2004, 21 pages.

Lindseth, Frank, et al., "Probe Calibration for Freehand 3D Ultrasound Reconstruction and Surgical Navigation", Dec. 2002, 27 pages.

Fuchs, Henry, et al., "Towards Performing Ultrasound-Guided Needle Biopsies from Within a Head-Mounted Display", University of North Carolina, Department of Computer Science, 1996, 10 pages; [Lecture Notes in Computer Science; vol. 1131 archive Proceedings of the 4th International Conference on Visualization in Biomedical Computing table of contents, pp. 591-600 Year of Publication: 1996, ISBN:3-540-61649-7; Hamburg, Germany, Sep. 22-25, 1996).].

Henry Fuchs, Andrei State, Mark A. Livingston, William F. Garrett, Gentaro Hirota, Mary Whitton and Etta D. Pisano (MD). "Virtual Environments Technology to Aid Needle Biopsies of the Breast: An Example of Real-Time Data Fusion." Proceedings of Medicine Meets Virtual Reality:4 (Jan. 17-20, 1996, San Diego, California), IOS Press, Amsterdam, Jan. 1996.

Rita StarBurst Soft Tissue Access System and RITA StarBurst Hard Tissue Access System, http://www.ritamedical.com, Rita Medical Systems, Inc., copyright 2002, , 8 pages.

Cool-tip RF Tissue Ablation System, Cool-tip RF System, and Cool-tip Electrodes, http://www.valleylab.com/static/cooltip/products.html, Valleylab, copyright 2004, 4 pages.

LeVeen Needle Electrode, Boston Scientific, printed from http://www.bostonscientific.com/med_specialty/deviceDetail.

ihtml?task= tskBasicDevice . . . , printed on Sep. 13, 2004, 1 page.

Bradford J. Wood et al., "Navigation with Electromagnetic Tracking for Interventional Radiology Procedures: A Feasibility Study", Laboratory Investigations, *Journal of Vasc. Interv. Radiol.*, vol. 16, 2005, pp. 493-505.

* cited by examiner

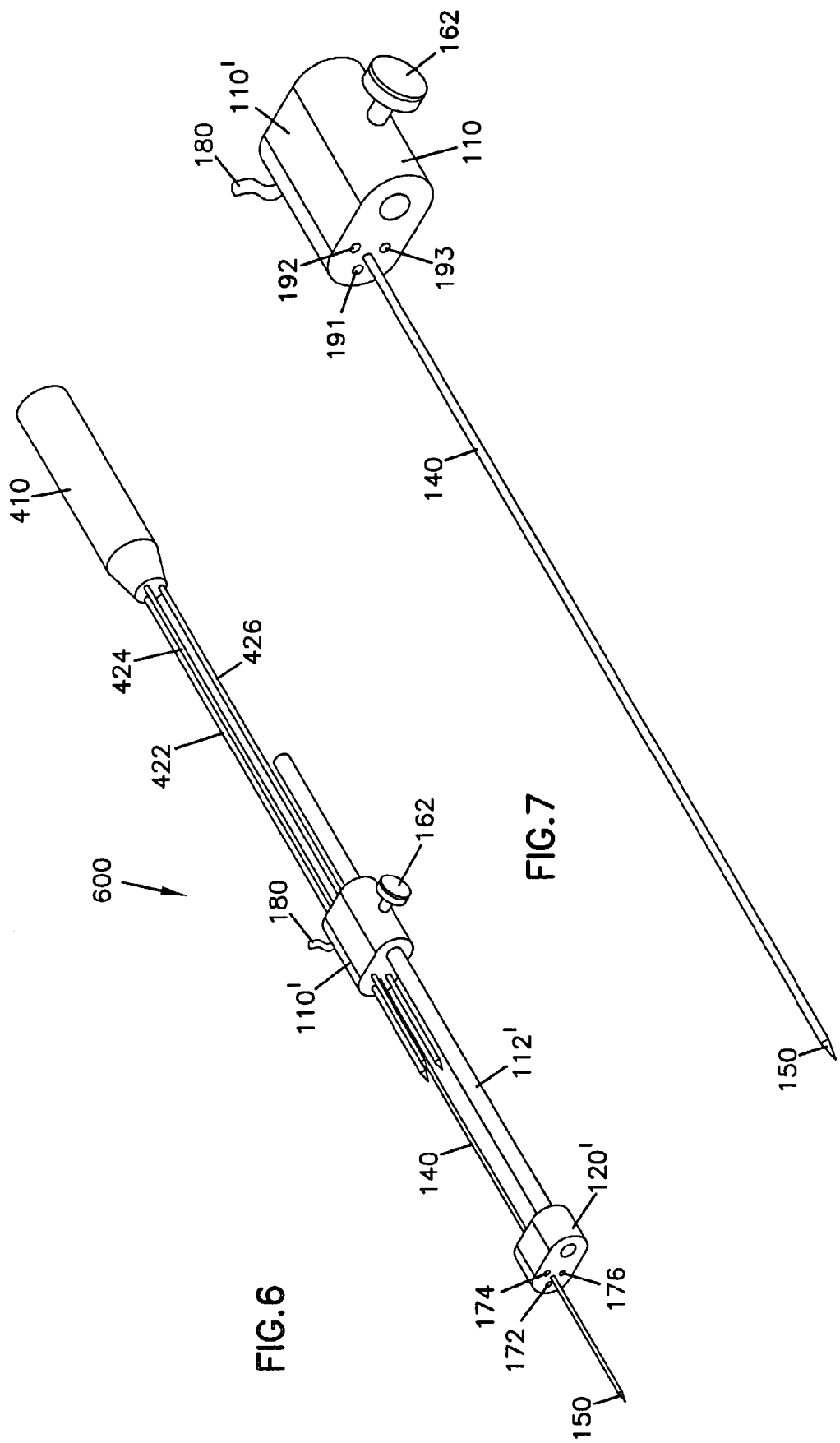

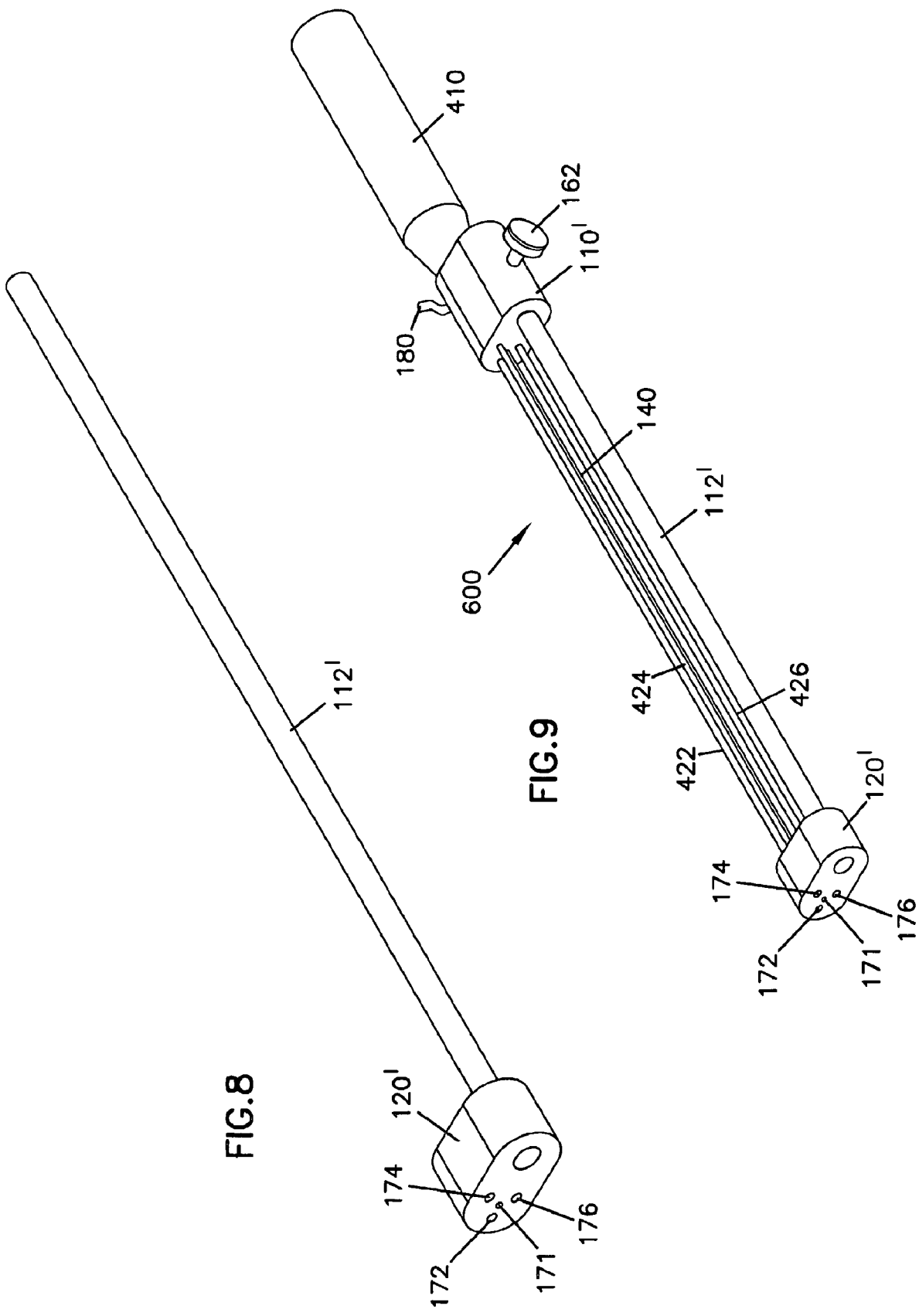

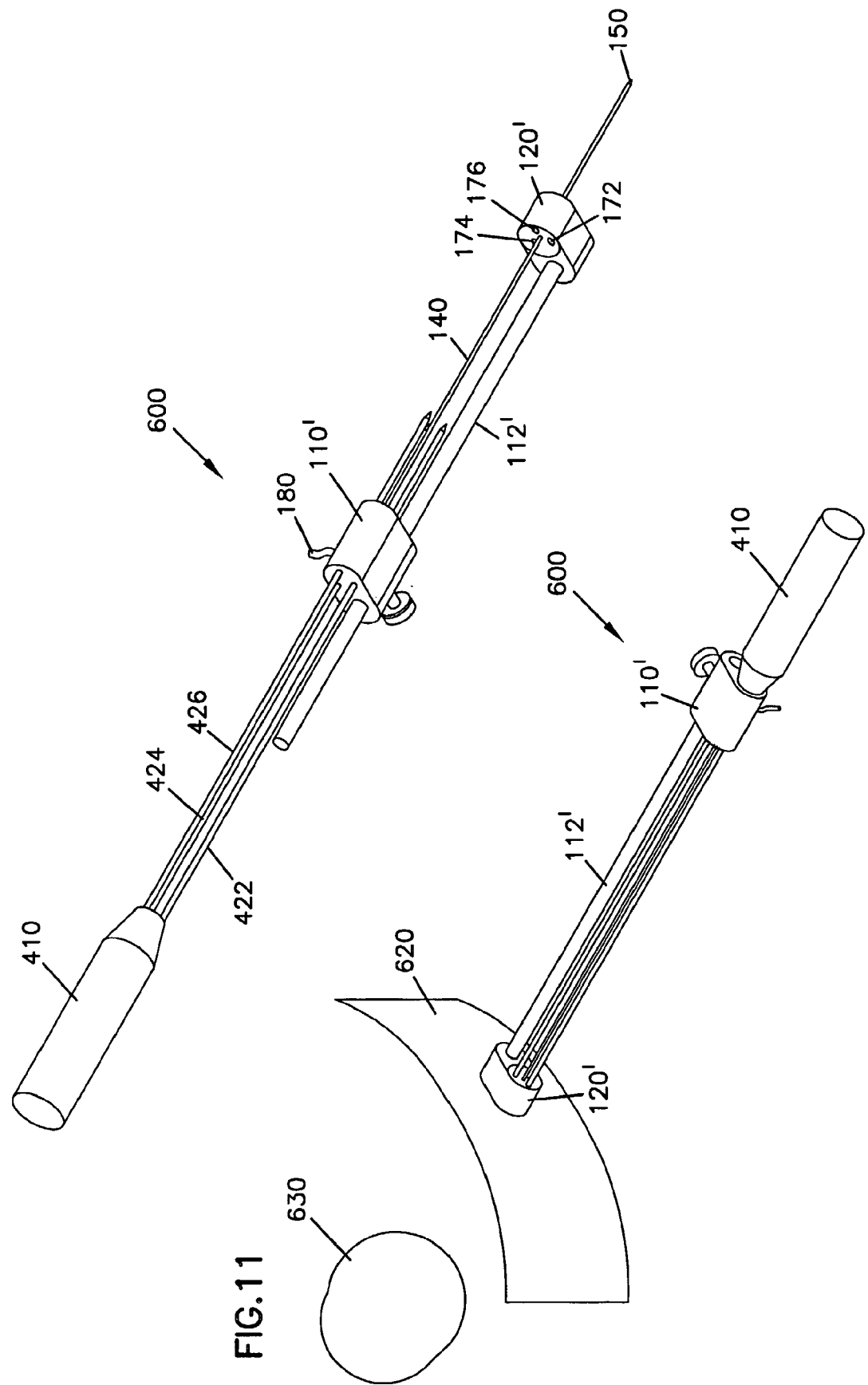

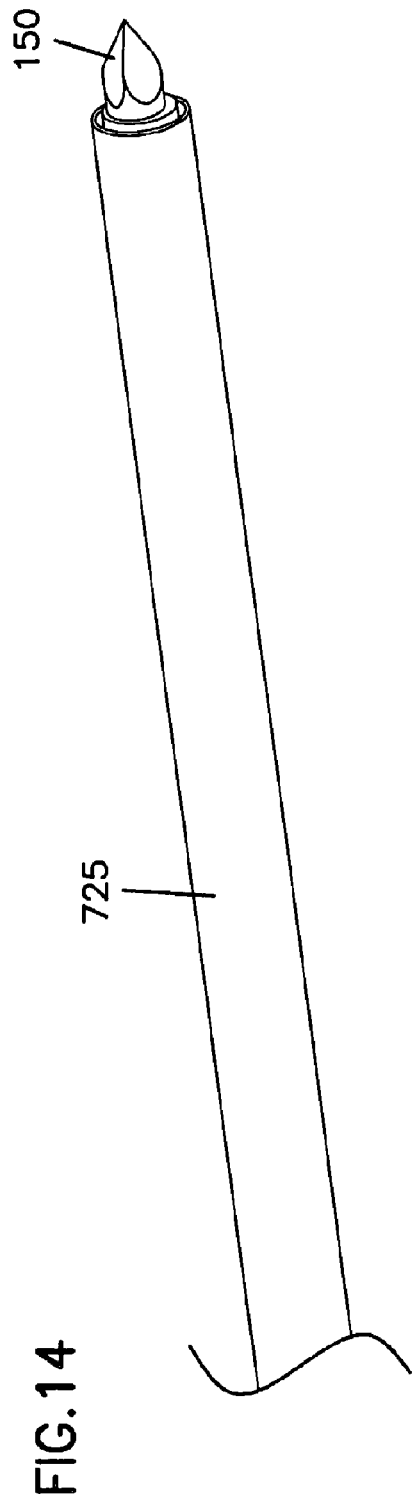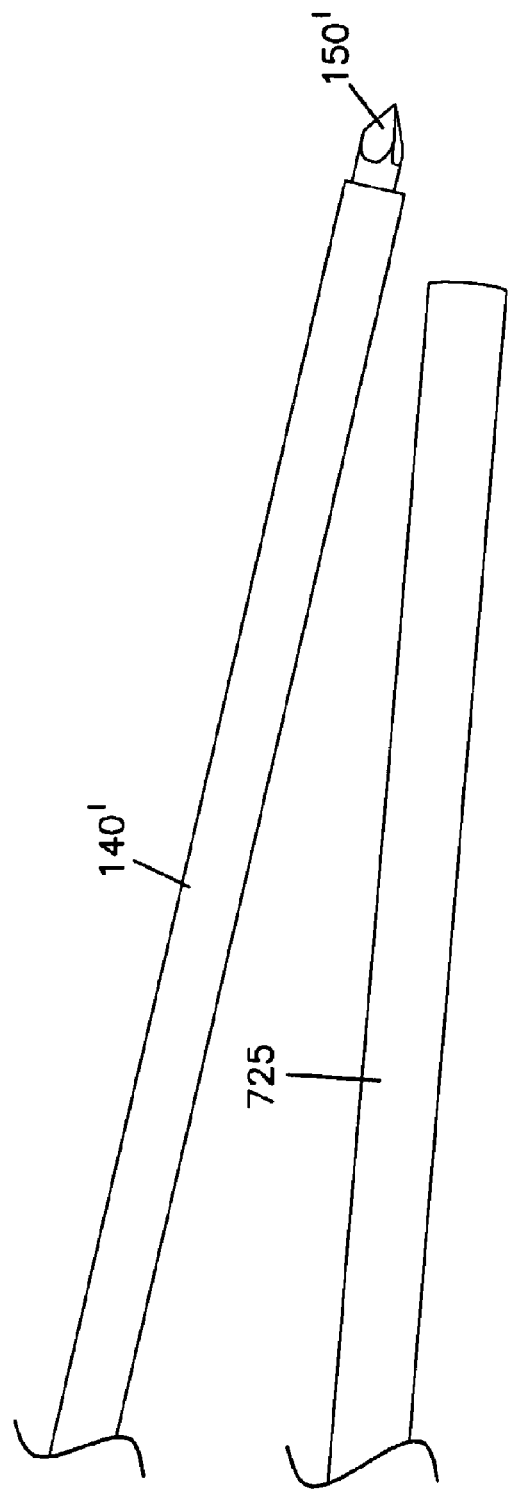

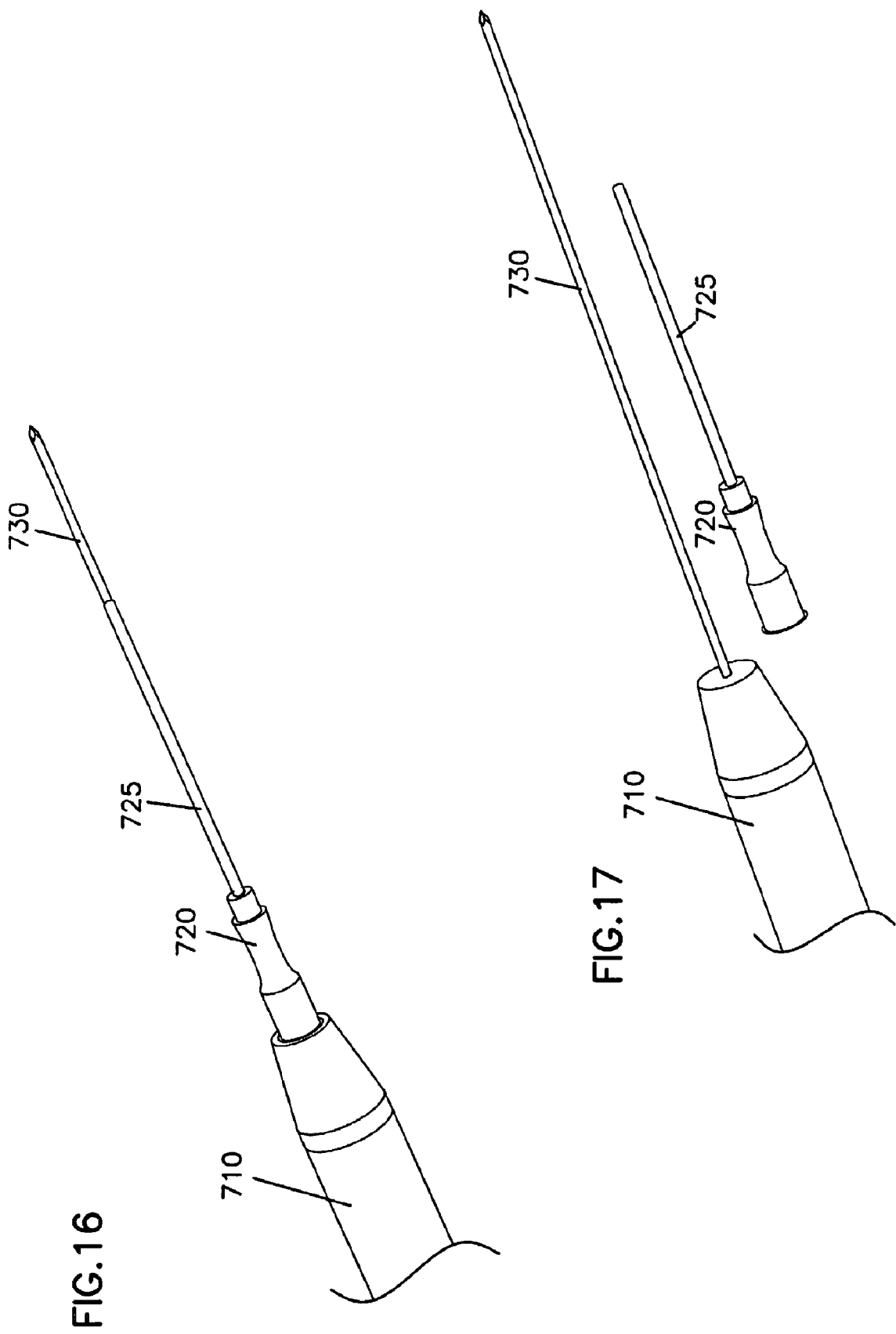

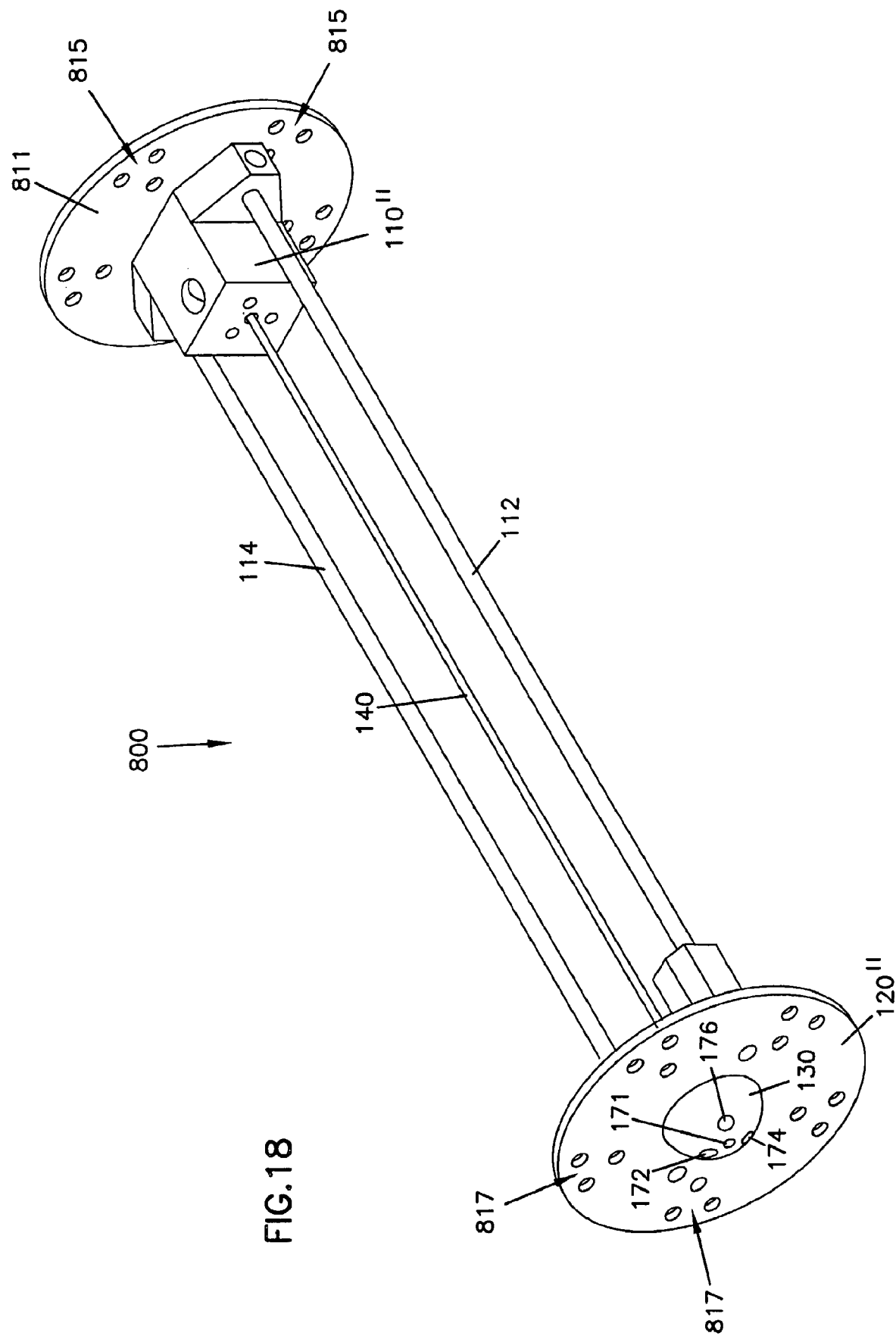

ACCESS SYSTEM

This application is being filed as a PCT International Patent Application on 4 Nov. 2005, in the name of The Government of the United States of America, as represented by the Secretary, Department of Health and Human Services, applicant for the designation of all countries except the U.S. and Bradford Johns Wood, and Neil Glossop, both U.S. citizens, applicants for the designation of the U.S. only, and claims priority to U.S. Application Ser. No. 60/625,186, filed 5 Nov. 2004.

STATEMENT REGARDING FEDERALLY SPONSORED RESEARCH OR DEVELOPMENT

The work performed during the development of this invention is supported by the Department of Health and Human Services. The Government of the United States of America may have certain rights in the invention disclosed and claimed herein below.

TECHNICAL FIELD

Embodiments disclosed herein generally relate to systems and methods for accessing internal structures of the body.

BACKGROUND

Minimally invasive surgical interventions are rapidly increasing in popularity. This is due to the development of new interventional techniques and the desire on the part of both clinicians and patients to decrease procedure-related morbidity and trauma. Minimally invasive interventions are done using catheters, needles, or other instruments that are introduced, targeted, and manipulated without the benefit of the direct instrument visualization afforded by the usual surgical exposure. Using such procedures minimizes trauma to the patient, but severely restricts the physician's view of the underlying anatomy. In contrast, image-guided surgery uses preoperative magnetic resonance imaging (MRI) or computed tomography (CT) scans to guide invasive surgical procedures, providing the physician with some guidance.

Typical image guided surgery systems are based on bony landmarks, especially with regard to applications in the brain and spine. One example of a device used for guiding invasive surgical procedures is seen in U.S. Pat. No. 5,558,091. The system described therein includes a magnetic positioning system that utilizes a reference probe, an instrument probe, and a magnetic field to magnetically track the instrument probe in the area of interest.

Other systems and methods that provide for efficient access of internal structures of the body are needed.

SUMMARY

Embodiments disclosed herein generally relate to systems and methods for accessing internal structures of the body.

According to one aspect, the invention relates to an access system including a needle, and a grid defining a plurality of guide apertures. The needle is inserted into and guided by one of the guide apertures of the grid as the needle is introduced into a body of a patient to a target site.

According to another aspect, the invention relates to an access system for a therapy or biopsy device, including a member including a semispherical surface defining an aperture, a hub defining an aperture and being slideably coupled to the member by a guide, and a lock mechanism configured to lock the hub relative to the member on the guide. The system also includes a removable probe that is inserted through the hub and the member, and a magnetically trackable sensor. The member is positioned against a surface, and the hub is slid relative to the plate along the guide until the sensor indicates that the probe is positioned at a target site.

According to another aspect, the invention relates to an access system for an ablation device. The system can include a plate with an aperture, a member coupled to the plate and including a semispherical surface, and a hub slideably coupled to the plate by a rod. The system can also include a lock mechanism configured to lock the hub relative to the plate on the rod, and a needle coupled to the hub, the needle including a magnetically trackable coil positioned in a tip of the needle. The semispherical surface of the member can be positioned against skin of a body and the hub slid relative to the plate along the rod to insert the needle through the aperture in the plate into the body until the tip reaches a target site. The hub can be locked by the lock mechanism when the tip of the needle reaches the target site and ablation energy delivered to the target site through the needle.

According to another aspect, the invention relates to a method of providing access to a target site in a body for ablation. The method can include: positioning a member including a semispherical surface against the body; sliding a hub relative to a stabilizing plate to introduce a needle into the body; magnetically tracking a tip of the needle as it moves through the body; locking the hub relative to the stabilizing plate when the needle reaches the target site; and introducing ablation energy to the target site through the needle.

DESCRIPTION OF THE DRAWINGS

FIG. 6 is a perspective view of another embodiment of an access system made in accordance with principles of the invention.

FIG. 7 is a perspective view of a hub and needle of the system of FIG. 6.

FIG. 8 is a perspective view of a stabilizing plate and rod of the system of FIG. 6.

FIG. 9 is a perspective view of the system of FIG. 6 including an example probe with a plurality of needles.

FIG. 10 is a perspective view of the system of FIG. 9 with the needle of the system and probe partially advanced.

FIG. 11 is a perspective view of the system of FIG. 6 with the system positioned against the skin of a patient adjacent to a target site.

FIG. 14 is a perspective view of a portion of an example cannula and needle.

FIG. 15 is a perspective view of the cannula and needle of FIG. 14.

FIG. 16 is a perspective view of an example probe introduced into the cannula of FIG. 15.

FIG. 17 is a perspective view of the cannula and needle of FIG. 16.

FIG. 18 is a perspective view of another embodiment of an access system made in accordance with principles of the invention.

DETAILED DESCRIPTION

Figure 1:
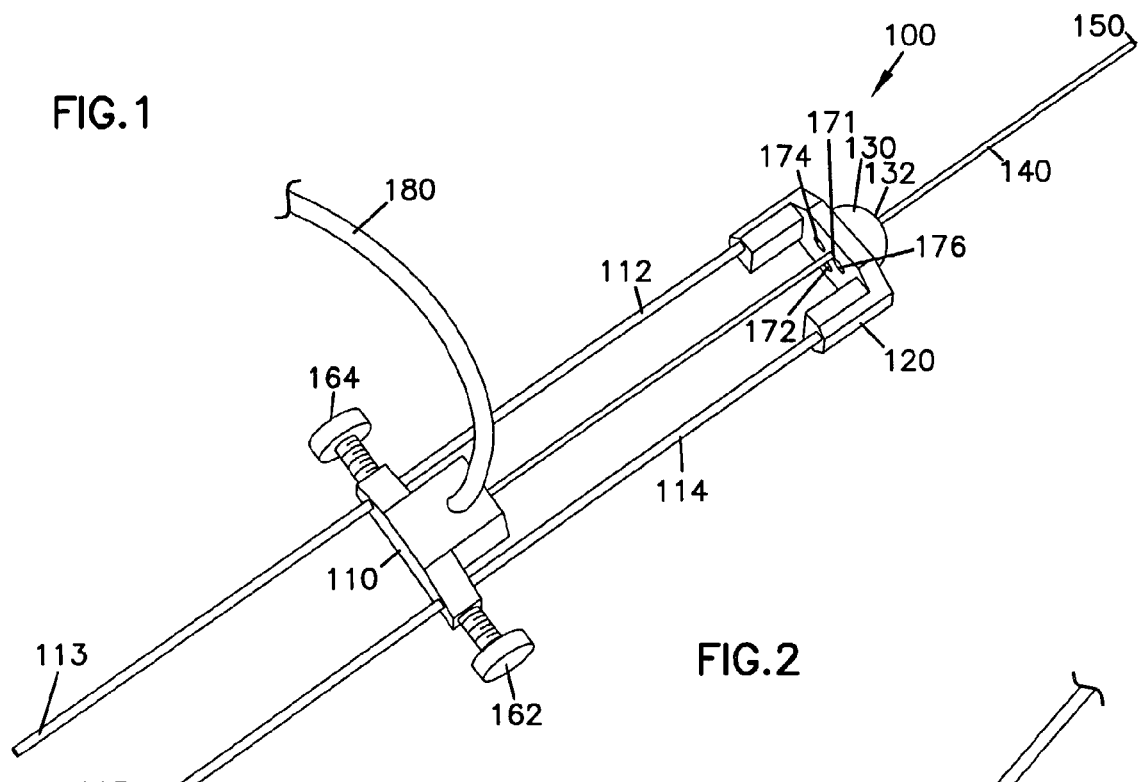
FIG. 1 is a perspective view of an embodiment of an access system made in accordance with principles of the invention.
Figure 2:
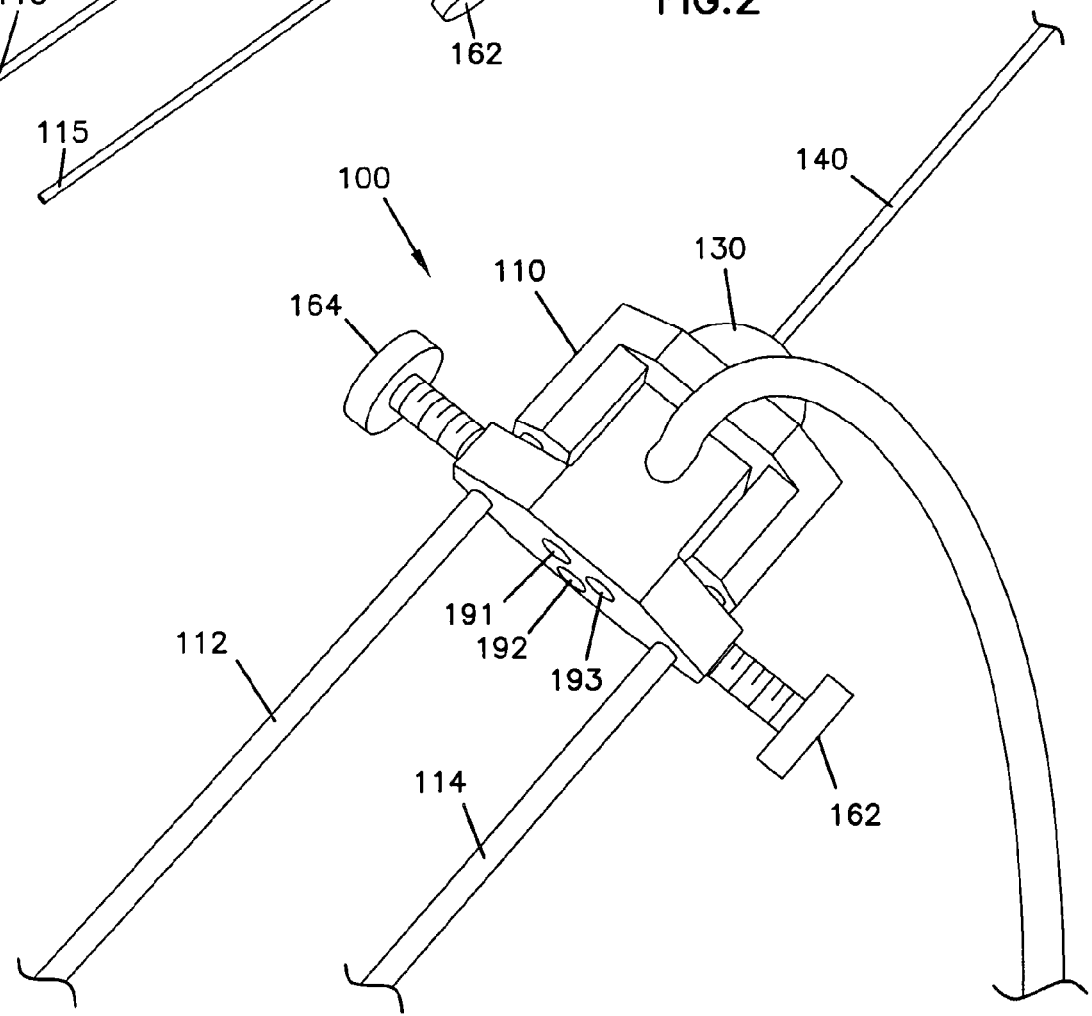
FIG. 2 is a perspective view of a portion of the system of FIG. 1 with a needle of the system in a fully inserted position.

Embodiments disclosed herein generally relate to systems and methods for accessing internal structures of the body.

In example embodiments, an access system is configured to access internal structures to provide therapy or to sample tissues, for example, for biopsy. Although many of the examples disclosed herein are referenced in relation to ablation therapy, the systems and methods are equally applicable to other types of therapy, as well as performing biopsies.

Example systems can include a member having a surface referred to herein as a button. The member allows the system to be pivoted and/or rotated against the body as the needle or probe is being positioned. Example systems also include a hub and a lock mechanism configured to lock the hub relative to the button on the rod.

Generally, the systems and methods disclosed herein also include the use of one more needles and/or probes of a system that are introduced into the body and tracked using, for example, electromagnetism. The needle and/or probe can be, for example, a leaking, injectable, deployable, or ablating needle. The needle and/or probe can be introduced into a target in the body, such as an organ, tumor, or tissue, to deliver therapy or to sample tissue. In some embodiments, a guide such as, for example, a grid is used to guide the needle and/or probe as it is introduced into the body.

Once in position, the needle and/or probe can be used to deliver therapy to the target in the body, or to sample tissue at the target site. Example therapies that can be delivered include radio frequency (RF), microwave, cryotherapy, chemotherapy, therapeutic molecules such as drugs, antibodies, growth factors the like, imaging agents such as radioactive compounds and antibodies conjugated to a detectable label, and ultrasonic. Ablation agents can include radiofrequency energy, cryogenic agents, hot water, chemotherapeutic agents, microwave energy, and ultrasound. Other types of therapies can also be delivered through the needle and/or probe. In addition, tissue sampling can be accomplished using the systems and methods described herein. Tissue samples can be used in methods including without limitation diagnostic, prognostic, monitoring of therapy, and automation of pharmocogenomic tools.

Referring now to FIGS. 1-5, an example system 100 for introducing a needle into a target in the body is shown. System 100 generally includes a hub 110, a stabilizing plate 120, a needle 140, and a conduit 180.

Hub 110 is slidingly coupled to plate 120 by a guide including rods 112 and 114. Specifically, hub 110 can slide from along rods 112, 114 towards or away from plate 120. For example, hub 110 can slide from ends 113 and 115 of rods 112, 114 towards plate 120. Retainer members 162 and 164 can have locked and unlocked positions to retain the hub 110 at a desired position relative to plate 120 on rods 112 and 114, as described below. Hub 110 also includes three apertures 191, 192, and 193 through which needles can be extended, as described below. More or fewer apertures can be included in alternative embodiments.

Plate 120 generally forms a guide or grid including a plurality of apertures 171, 172, 174, and 176 through which one or more needles can be inserted. The apertures 171, 172, 174, and 176 function to hold and guide the needles as the needle are inserted into the body to a target site.

Specifically, plate 120 includes central aperture 171 through which needle 140 extends. Plate 120 also includes apertures 172, 174, and 176 through which additional needles can be extended, as described below. Plate 120 further includes a button 130. In some embodiments, the plate 120 and button 130 are formed as a single piece. In other embodiments, the plate 120 and button 130 are formed as separate pieces that are coupled together.

In some embodiments, button 130 includes a surface 132 that can be placed against the skin of the patient. In example embodiments, surface 132 of button 130 is semispherical or rounded. Surface 132 of the button 130 provides for stabilization of system 100 against the skin of the patient, while still allowing the angle of insertion of needle 140 to be modified by moving surface 132 against the skin of the patient to a desired position.

Needle 140 extends through an apex of button 130 as needle 140 extends through plate 120. Needle 140 is coupled to hub 110 and, as previously noted, extends through aperture 171 of plate 120. In some embodiments, needle 140 is removable from hub 110, while in others needle 140 is fixed to hub 110. In the example embodiment shown, a distal end 150 of needle 140 includes a sensor coil 310 embedded therein. See FIG. 3. In example embodiments, the needle 140 and sensor coil 310 are configured as described in U.S. Pat. No. 6,785,571 to Glossop, the entirety of which is hereby incorporated by reference.

In some embodiments, sensor coil 310 is positioned in one or more needles that are introduced into the body and positioned at one or more target sites. In other embodiments, the sensor coil 310 can be included in one or more probes that are introduced into the body and positioned at the target site to, for example, provide therapy (e.g., RF, microwave, cryotherapy, and/or ultrasonic). Example needles and probes can be single or multi-lumen. Example needles include biopsy needles and brachytherapy needles. Example probes include RF ablation probes, microwave probes, optical coherence tomography (OCT) probes, laser probes, ultrasound probes, and cryogenic probes. In other embodiments, a hollow cannula or an electrode can also be used. Other probe configurations and geometries can be used. For example, in alternative embodiments, probes including microwave ring antennae, deployable arrays, or cryogenic probe grids can be used.

Figure 3:
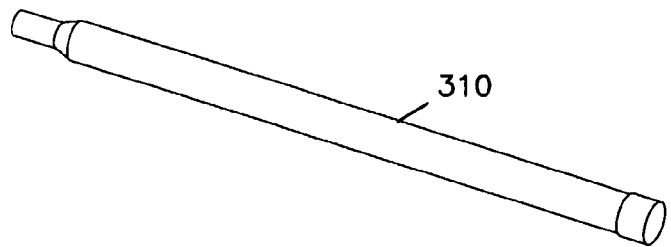
FIG. 3 is a perspective view of an embodiment of a sensor coil made in accordance with principles of the invention.
Figure 3A:
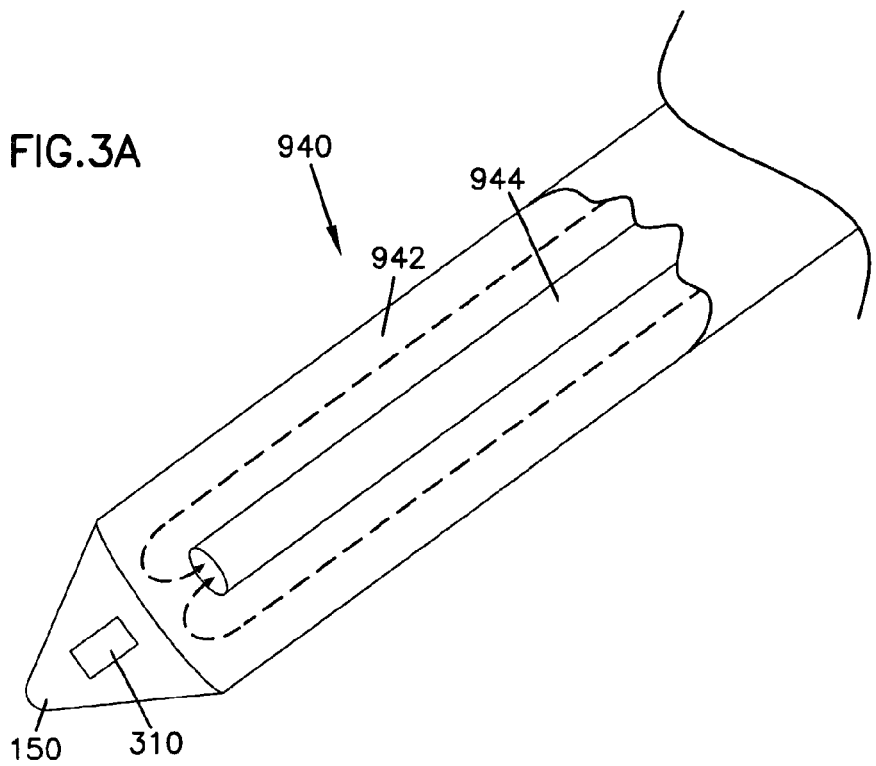
FIG. 3A is a perspective view of a portion of an embodiment of a probe with a portion of the probe shown in cross-section and including the example sensor coil shown in FIG. 3.

For example, a portion of an example probe 940 for delivering RF therapy is shown in FIG. 3A. Probe 940 is hollow and includes a solid pointed end 150. Sensor coil 310 can be embedded in end 150 as shown. In other embodiments, sensor coil 310 can be positioned in one or more of the conduits 942 and 944 formed in probe 940. Other configurations are possible. For example, in other embodiments, the sensor coil can be coaxially coupled to the probe, placed in tandem or parallel to the probe, or delivered by a guide used to guide the probe.

Figure 3B:
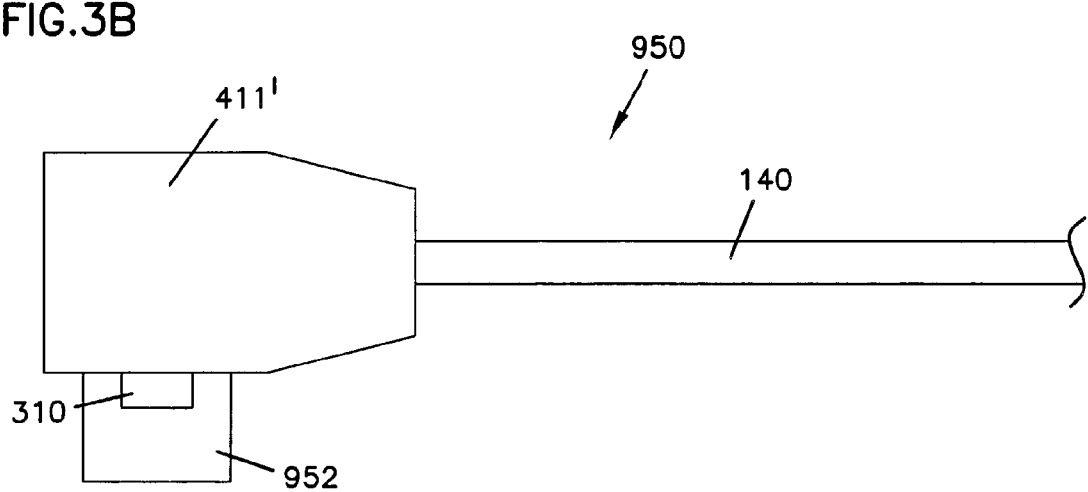
FIG. 3B is a side view of a portion of an embodiment of a probe including the example sensor coil shown in FIG. 3.
Figure 4:
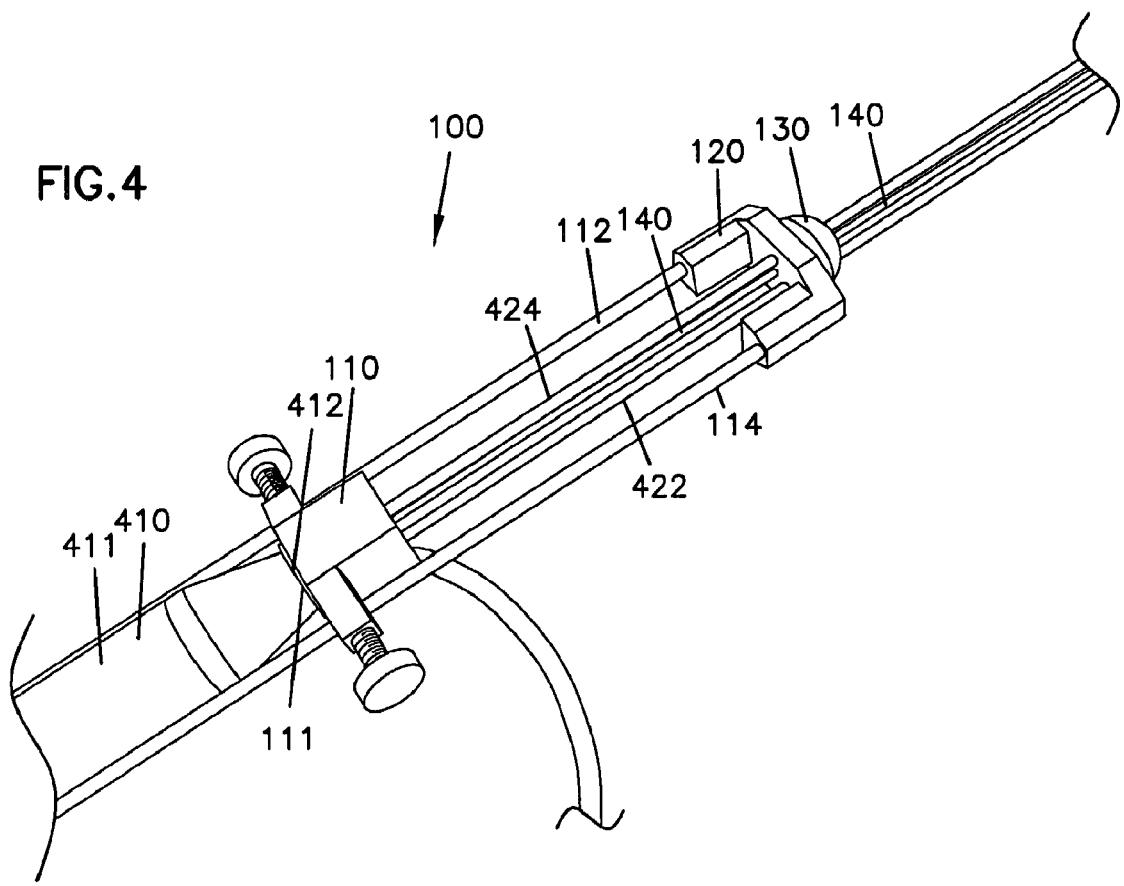
FIG. 4 is perspective view of a portion of the system of FIG. 1 including an example probe with a plurality of needles.

In yet other embodiments, the coil 310 is positioned at a handle of a probe or needle. For example, as shown in FIG. 3B, coil 310 is coupled to handle 411' of probe 950. In the example shown, coil 310 is coupled to handle 411' by a clip 952. In other embodiments, coil 310 can be coupled to handle 411' using other methods such as, for example, other fasteners including adhesives and screws, or coil 310 can be embedded in handle 411'. In yet other embodiments, coil 310 can be coupled to or otherwise positioned in hub 110.

As described further below, coil 310 can be electromagnetically tracked using an electromagnetic tracking system such as, for example, the AURORA™ system manufactured by Northern Digital Inc. of Ontario, Canada, so that the position of end 150 can be tracked as needle 140 is introduced into the body. Examples of similar sensors and systems to use such sensors can be found in U.S. Pat. No. 6,288,785 to Frantz et al., the entirety of which is hereby incorporated by reference. In addition, the needle and/or probe can include an echogenic coating that can be tracked using ultrasound. Needles or probes can also include coatings that provide for elution of therapeutic agents at the site.

In the example embodiment shown, the lengths of needle 140 and rods 112 and 114 are sized so that system 100 can be positioned against the skin of the patient and needle 140 can be inserted into a target site in the body of the patient. For example, the length of needle 140 and rods 112 and 114 can be configured so that the target site is reached by end 150 of needle 140 before hub 110 contacts plate 120. Longer or shorter needles and/or rods can be used, as desired, to extend or shorten the length of insertion of the needle.

Figure 5:
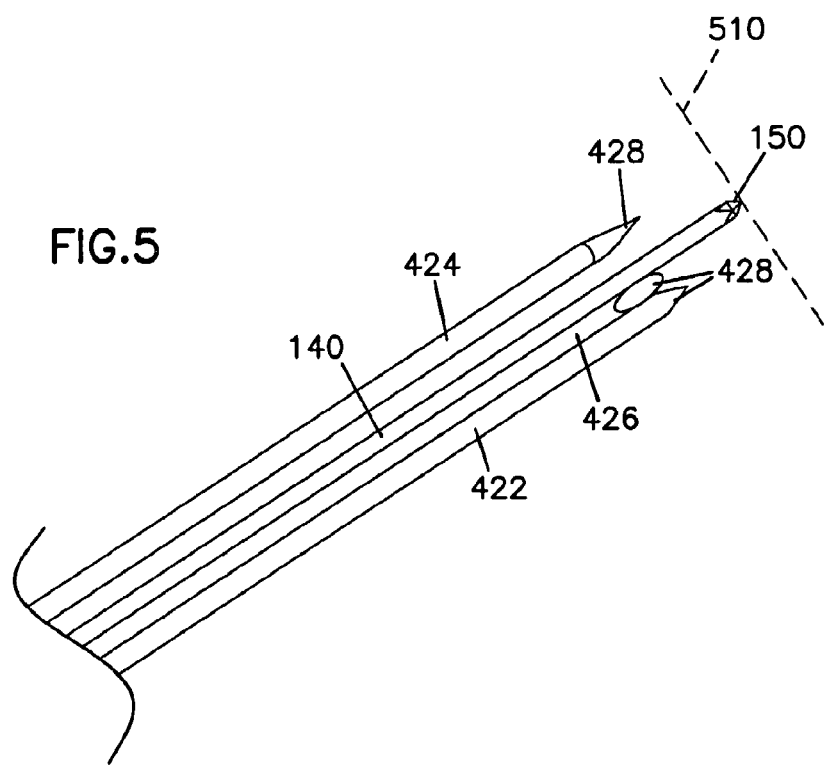
FIG. 5 is a perspective view of a portion of needles of the system of FIG. 4.
Figure 12:
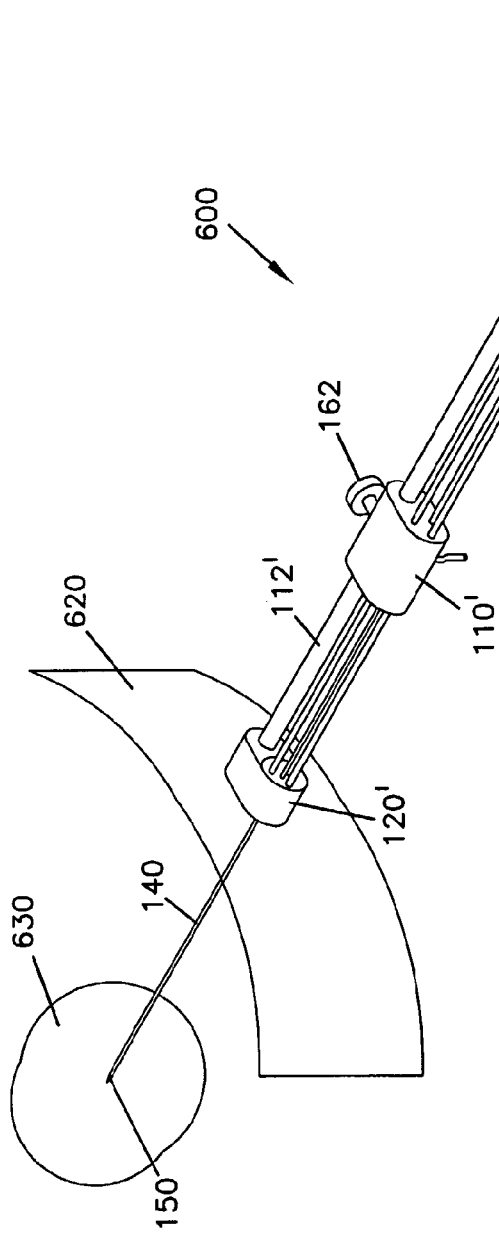
FIG. 12 is a perspective view of the system of FIG. 11 with the needle of the system advanced to the target site and a probe partially advanced.
Figure 13:
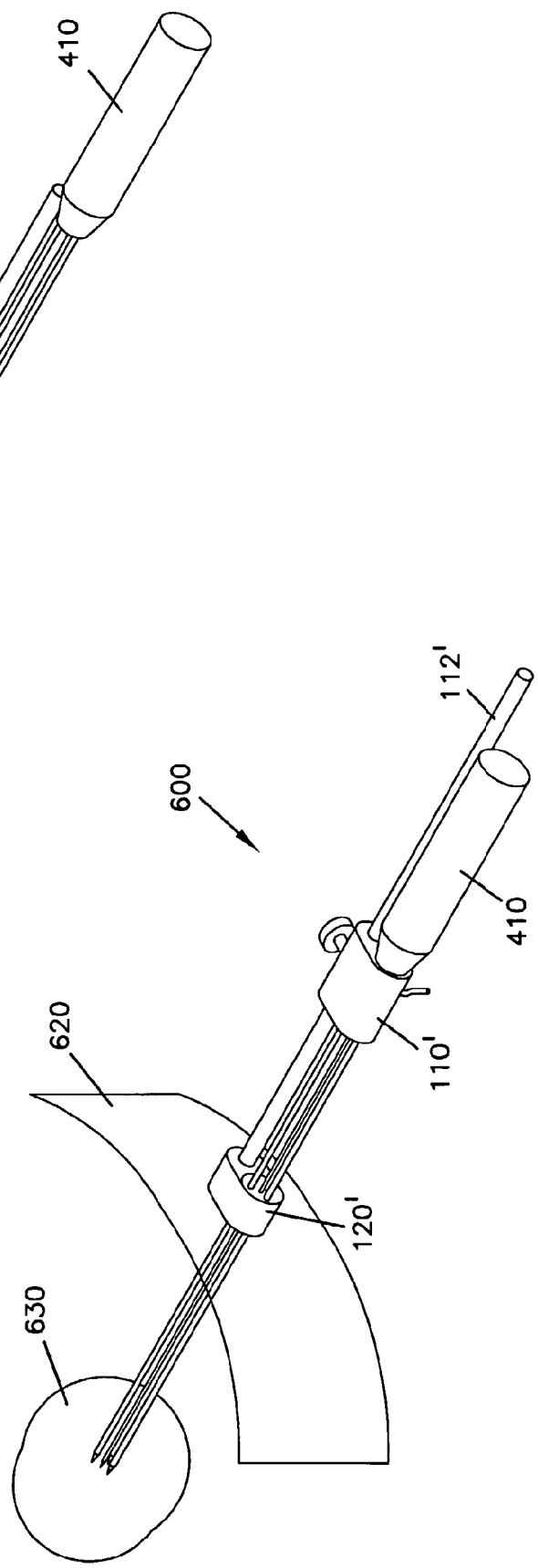
FIG. 13 is a perspective view of the system of FIG. 12 with needles of the probe fully advanced to the target site.
Figure 19:
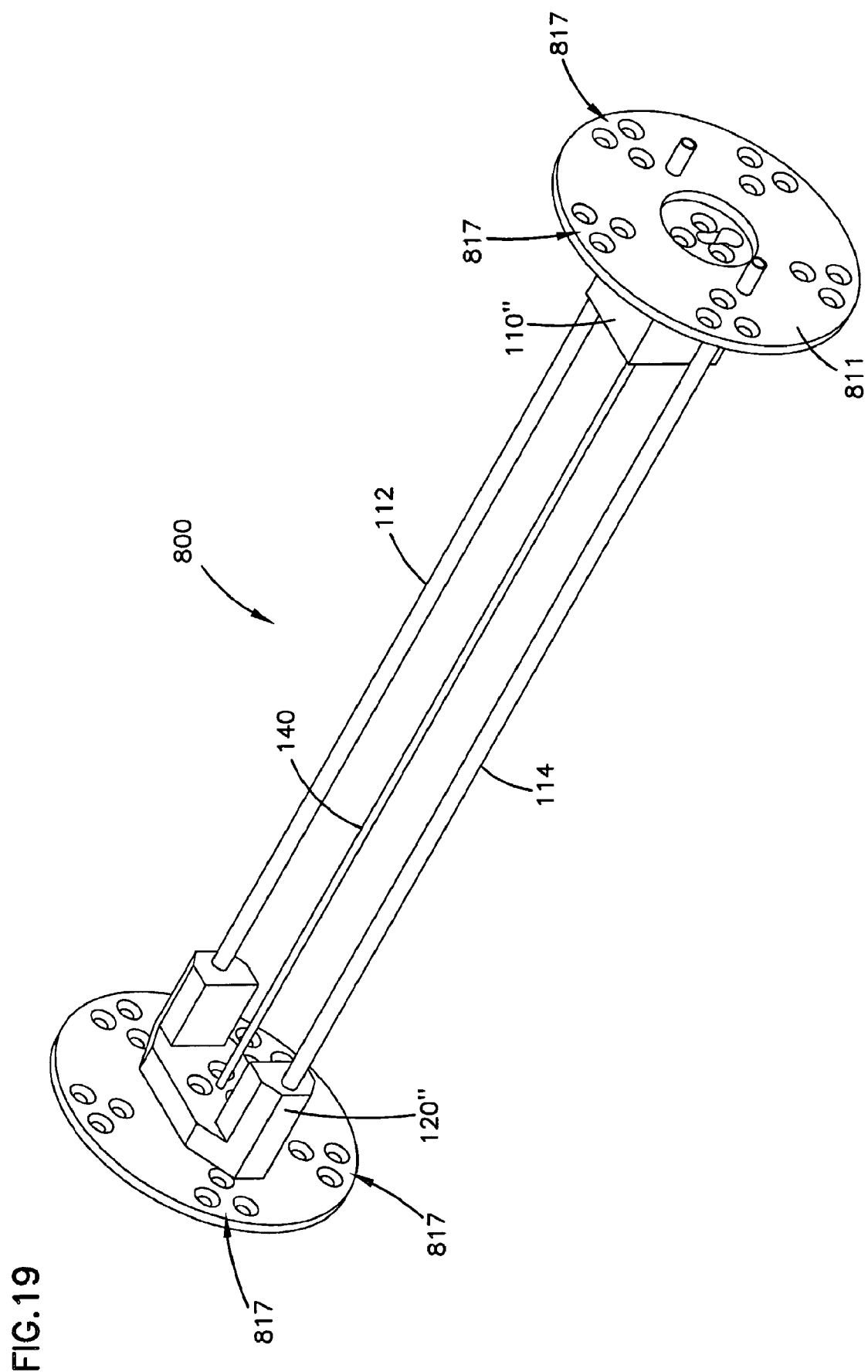
FIG. 19 is an opposite perspective view of the system of FIG. 18.
Figure 20:
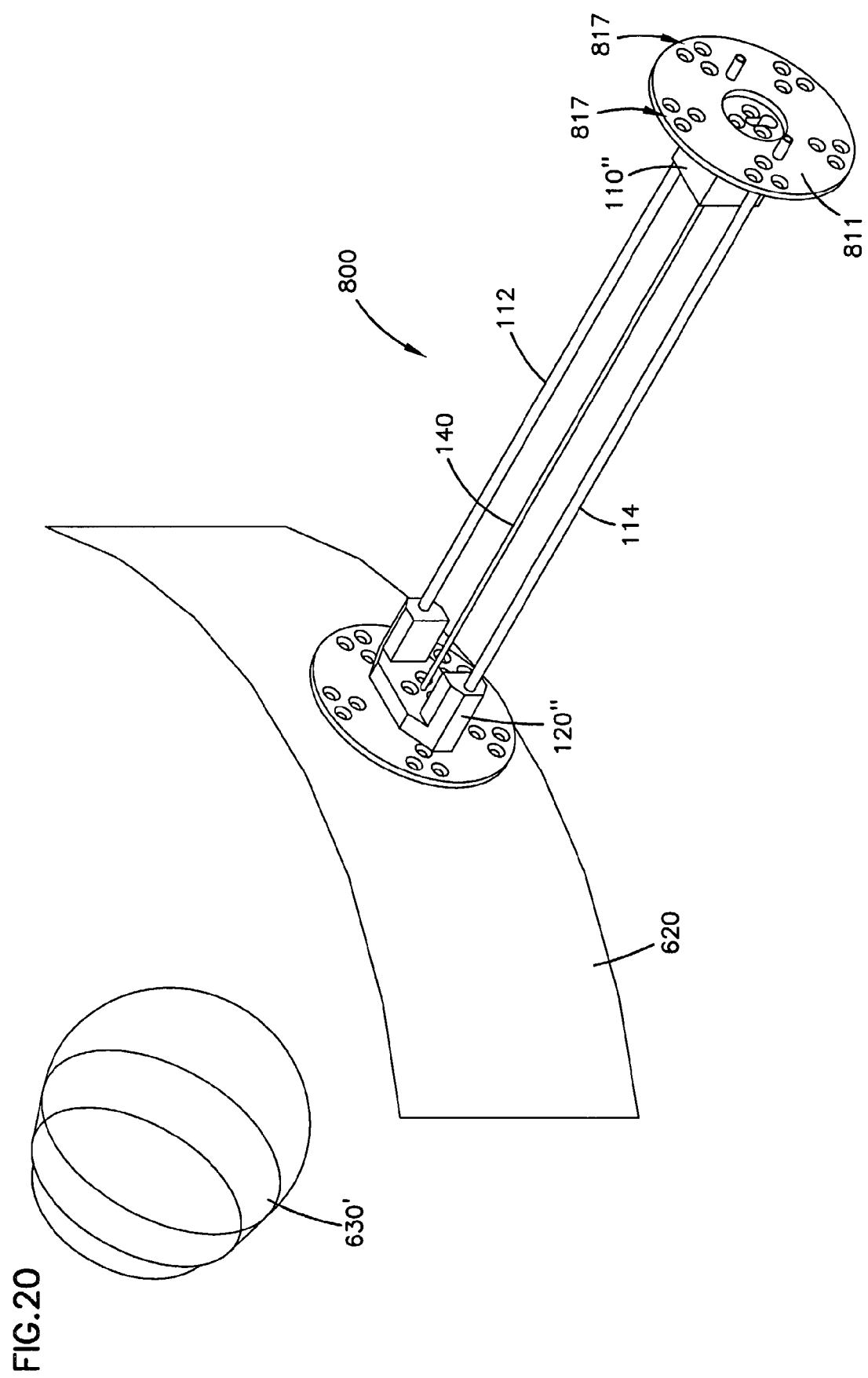
FIG. 20 is a perspective view of the system of FIG. 18 with the system positioned against the skin of a patient adjacent a target site.
Figure 21:
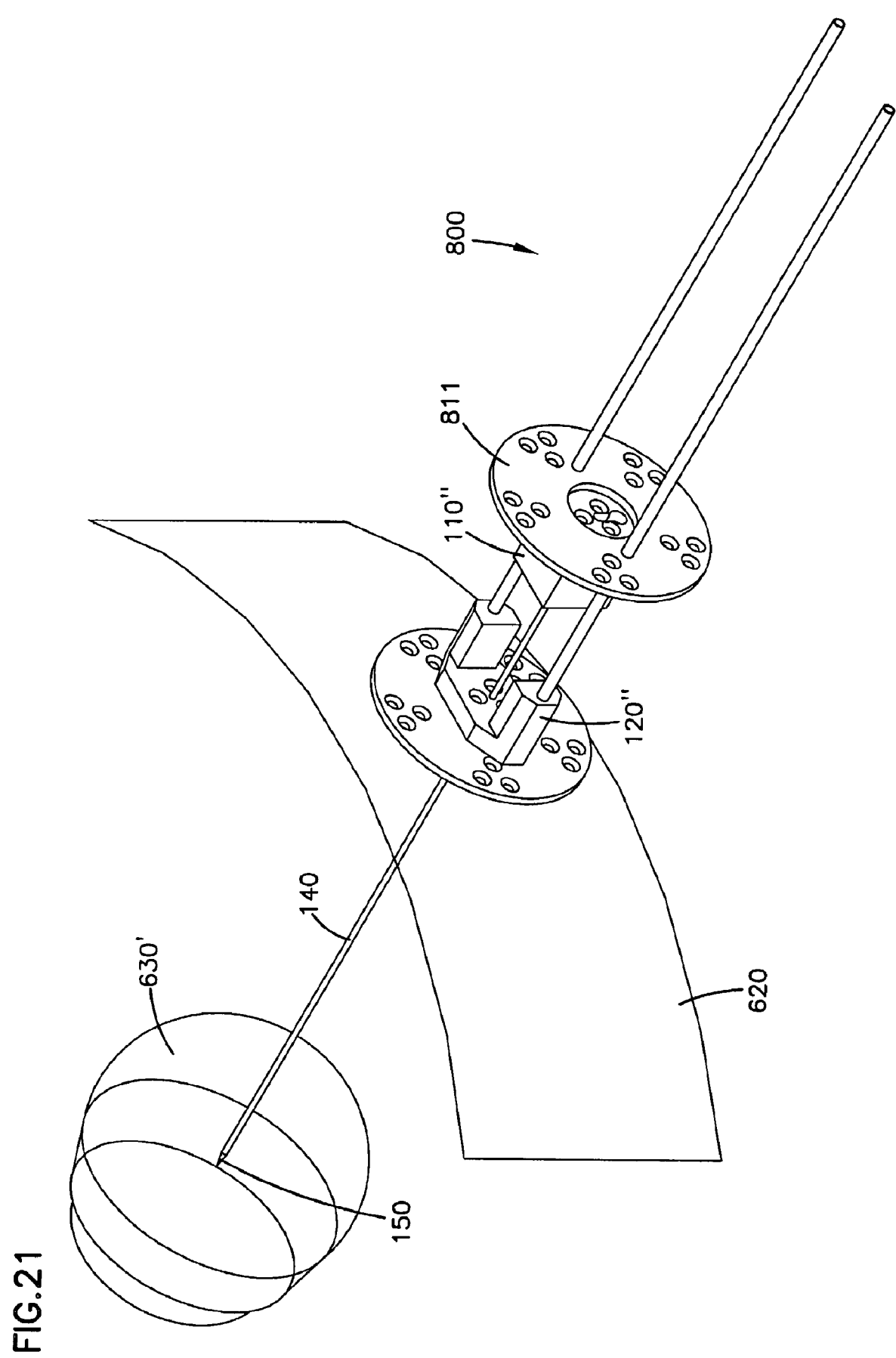
FIG. 21 is a perspective view of the system of FIG. 20 with a needle of the system advanced to the target site.
Figure 22:
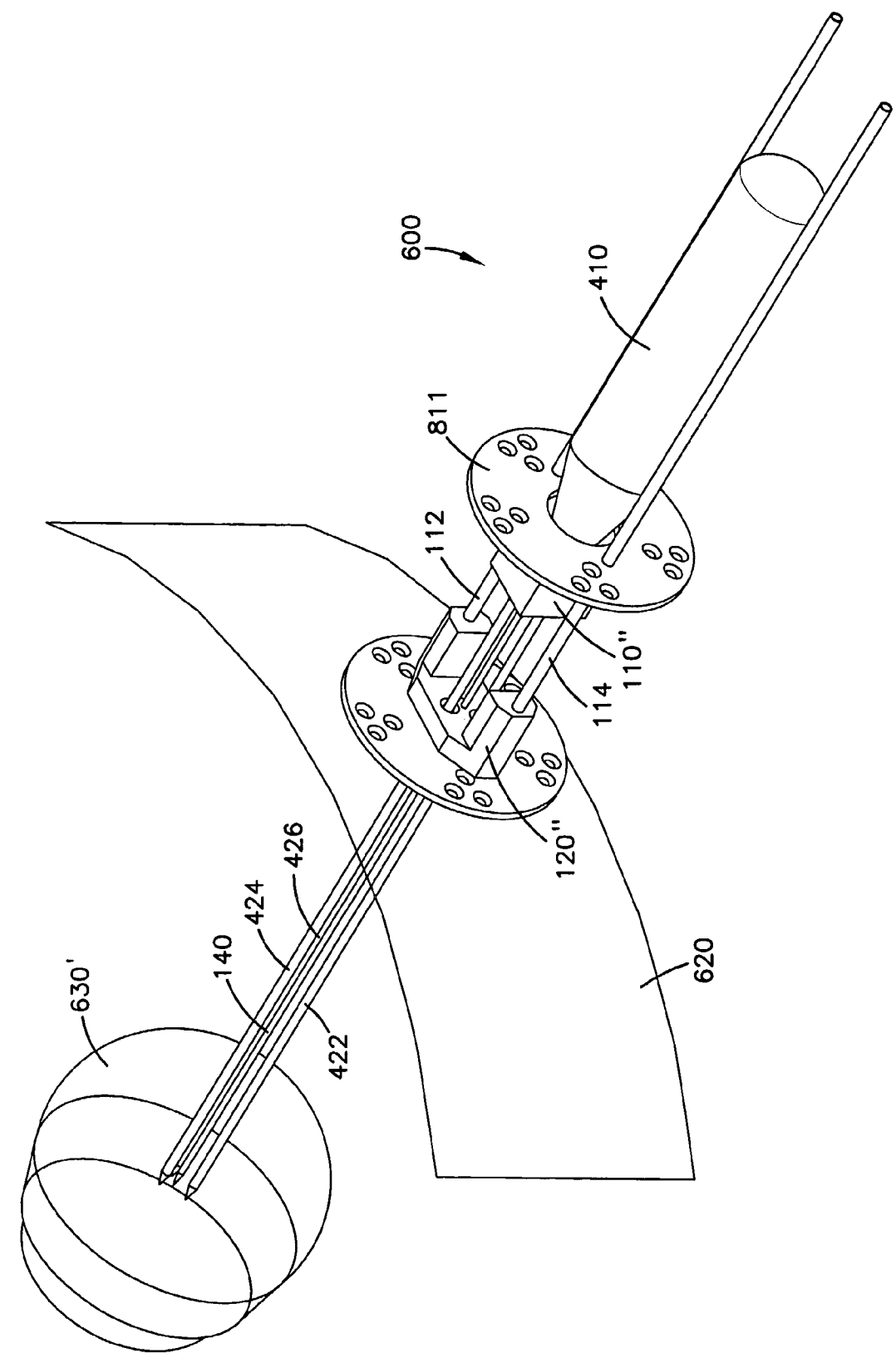
FIG. 22 is a perspective view of the system of FIG. 21 with needles of a probe fully advanced to the target site.
Figure 23:
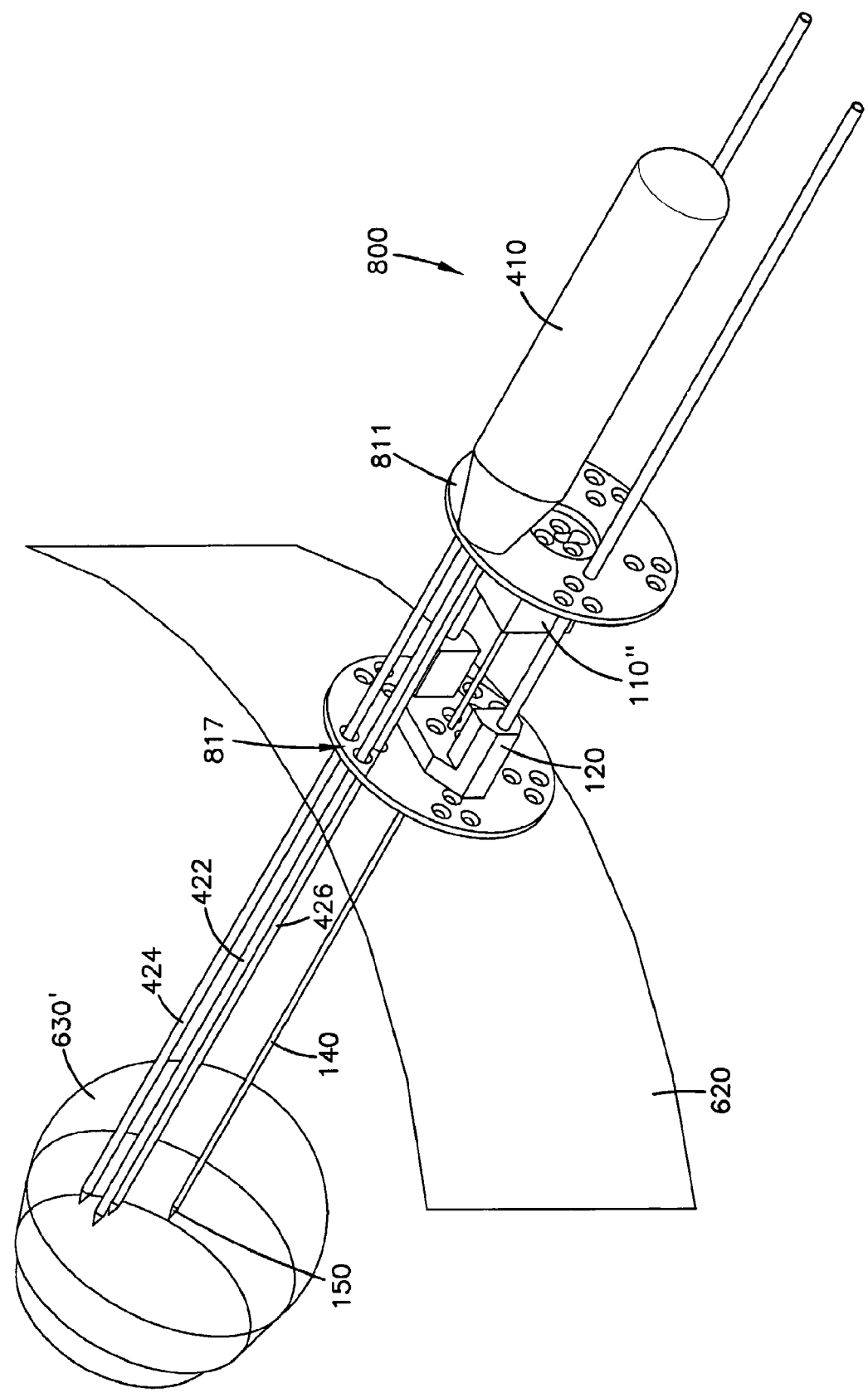
FIG. 23 is a perspective view of the system of FIG. 22 with needles of a probe fully advanced through a different set of apertures to the target site.

System 100 also includes a probe 410 including a handle 411 and three needles 422, 424, and 426 extending therefrom. Probe 410 is shown with needles 422, 424, and 426 extended through the apertures formed in hub 110, plate 120, and button 130. In the embodiment shown in FIG. 4, probe 410 is configured so that, when an end 412 of handle 411 contacts a surface 111 of hub 110, needles 422, 424, and 426 extend through plate 120 at the same approximate length as the needle 140. Therefore, when end 412 of handle 411 contacts surface 111 of hub 110, ends 428 of needles 422, 424, and 426 extend to approximately a plane 510 running perpendicular to end 150 of needle 140. In FIG. 5, probe 410 has not been inserted fully so that end 412 contacts surface 111 and therefore ends 428 of needles 422, 424, and 426 do not extend completely to plane 510.

In other embodiments, probe 410 can include a stop that limits the distance the probe can be inserted into hub 110. For example, in one embodiment, the stop can include an increase in a diameter of the probe 410 so that, at the increased diameter stop, the probe 410 cannot be inserted further through apertures in hub 110.

In the example shown, needles 422, 424, and 426 are located approximately 5 millimeters apart from one another. In this manner, needles 422, 424, and 426 are geometrically positioned a known distance from needle 140 and therefore allow needles to be inserted in known positions adjacent to the target site. This can allow for ease, for example, in ablating sections of larger tumors that exhibit a large target site. In other embodiment, needles 422, 424, and 426 can be located closer together or farther apart. In addition, in some embodiments, more or few needles can be provided on probe 410.

Probes of different configurations can be used depending on the type of ablation that is being done. For example, as noted above, different probes can be used to perform RF, microwave, cryotherapy, and/or ultrasonic therapies. Needles of the probes are used to deliver the ablation energy or an ablation agent to the target site. In addition, probes having needles of differing lengths can also be used to access different regions adjacent to the target site.

Conduit 180 is coupled through hub 110 to needle 140. Conduit 180 can be used, for example, to deliver a signal from sensor coil 310 or to deliver ablation energy or agent through needle 140 to a target.

System 100 can generally be used as follows. Initially, needle 140 is in its fully retracted position with hub 110 positioned at ends 113 and 115 of rods 112 and 114 so that needle 140 is retracted within button 130. Button 130 is placed on the skin of the patient at a desired location, and the angle of system 100 relative to the patient's body can be manipulated using the surface 132 of button 130 until a desired entry angle is reached. For example, surface 132 of button 130 can be pivoted and/or rotated relative to the patient's body. In example embodiments, system 100 can be pivoted about surface 132 of button 130 against the patient's body so that the angle of entry for needle 140 relative to the patient's body ranges from approximately 0 to 180 degrees. In addition, system 100 can be rotated about surface 132 of button 130 against the patient's body so that the orientation of the needle 140 relative to the patient's body ranges from 0 to 360 degrees.

Members 162 and 164 are unlocked to allow hub 110 to slide towards plate 120 along rods 112 and 114 to introduce needle 140 into the patient's body. As needle 140 enters and travels through the body to a target location, sensor 310 in end 150 of needle 140 can be tracked using, for example, an electromagnetic tracking system such as the AURORA™ system manufactured by Northern Digital Inc. of Ontario, Canada. The signal from sensor 310 may be delivered back to the electromagnetic tracking system via conduit 180. Once end 150 of needle 140 is in a desired target position within the body, members 162 and 164 are locked so that hub 110 and needle 140 are maintained at the desired location.

Next, an ablation agent such as RF, microwave, cryotherapy, and/or ultrasonic is introduced by conduit 180 through needle 140 to the target location positioned adjacent to end 150 of needle 140. In addition, probe 410 can be introduced by sliding needles 422, 424, and 426 through the apertures formed in hub 110 and plate 120 to positions adjacent to the target location at end 150 of needle 140. Additional ablation agents can be introduced through one or more of needles 422, 424, and 426 to further ablate tissue surrounding needles 422, 424, and 426.

Referring now to FIGS. 6-13, another embodiment of a system 600 for introducing a needle into a target in the body is shown. System 600 is similar to that of system 100 described above. However, system 600 includes only a single rod 112' along which hub 110' slides. In addition, no button is provided on plate 120'. Instead, plate 120' is placed against skin 620 before needle 140 is introduced into the body to a target site 630. See FIGS. 11-13.

Referring now to FIGS. 14-17, another embodiment of a needle 140' for introduction into a target in the body is shown. Needle 140', which may be tracked with a sensor coil, is ensheathed by a cannula 725 of a member 720. Once the needle 140' and cannula 725 are positioned at the target site in the body, needle 140' can be removed from cannula 725, and a needle 730 of a probe 710 can be introduced through needle cannula 725 to the target site. Ablation energy can then be introduced through needle 730 to the target site.

Referring now to FIGS. 18-23, another embodiment of a system 800 for introducing a needle into a target in the body is shown. System 800 is similar to systems 100 and 600 described above. However, system 800 includes a hub 110'' having a stabilization plate 811 coupled thereto. Plate 811 includes a plurality of sets of apertures 815 through which needles of a probe can be inserted. In addition, plate 120'' includes a plurality of sets of apertures 817 corresponding to sets 815 of plate 811. In the example shown, five sets of apertures 815 and 817 are provided.

System 800 is used as follows. Needle 140 is introduced into skin 620 until target 630' is reached. See FIG. 21. Probe 410 can then be inserted into apertures 172, 174, and 176 surrounding central aperture 171 through which needle 140 extends. See FIG. 22. In addition, probe 410 can be inserted into one or more of the sets of apertures 815 and 817 on plates 811 and 120'' to thereby cover a larger area adjacent to the target site. See FIG. 23.

Figure 24:
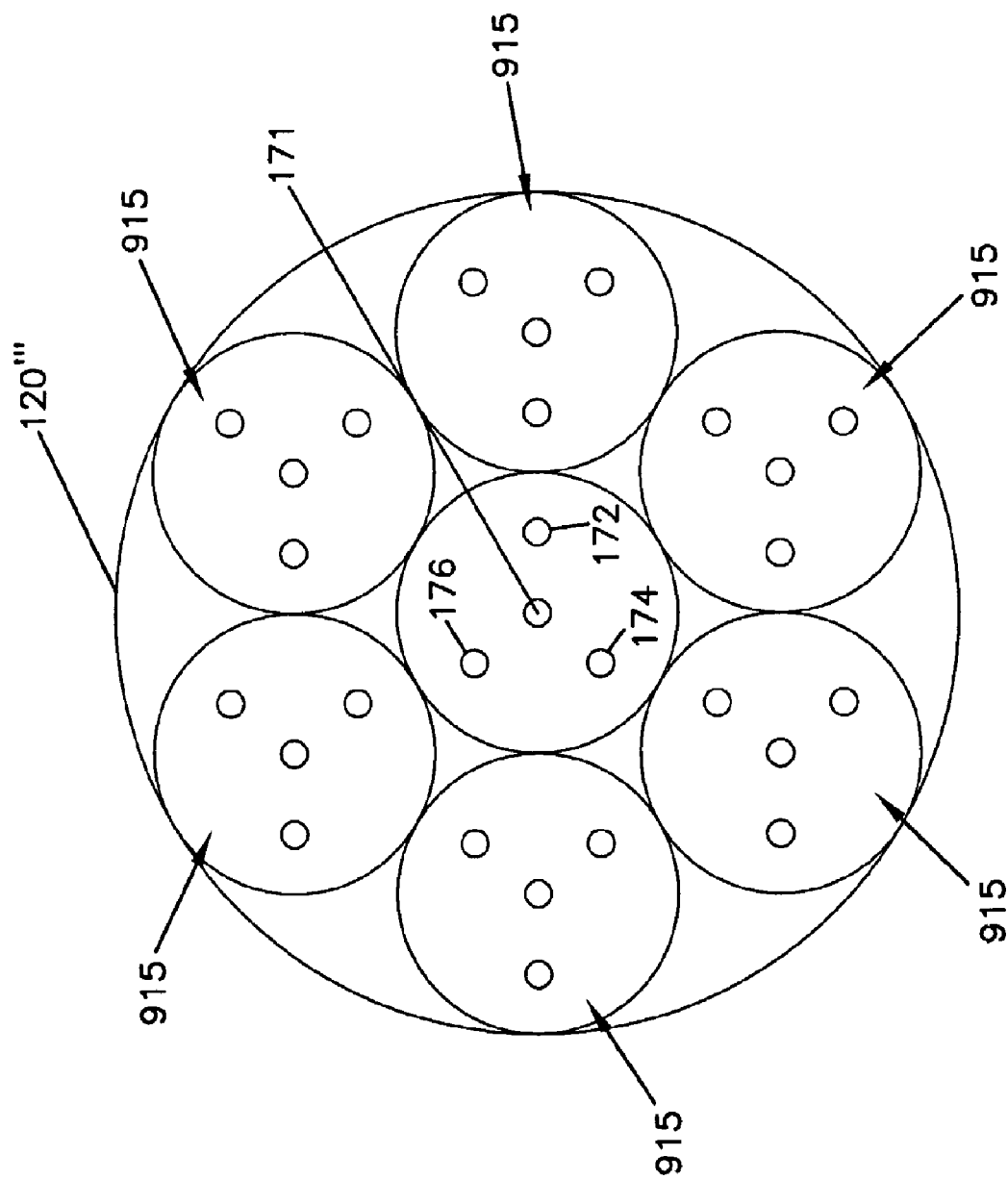
FIG. 24 is an end view of an embodiment of a stabilizing plate made in accordance with principles of the invention.
Figure 25:
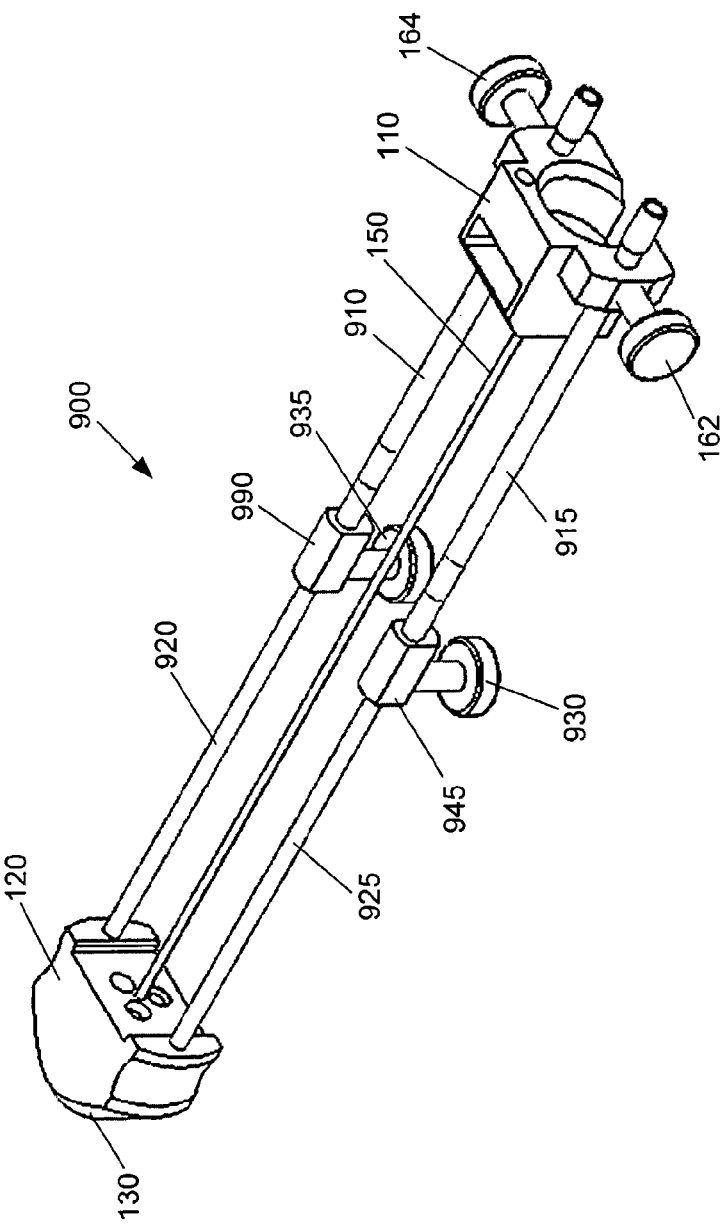
FIG. 25 is a perspective view of another embodiment of an access system made in accordance with principles of the invention.
Figure 26:
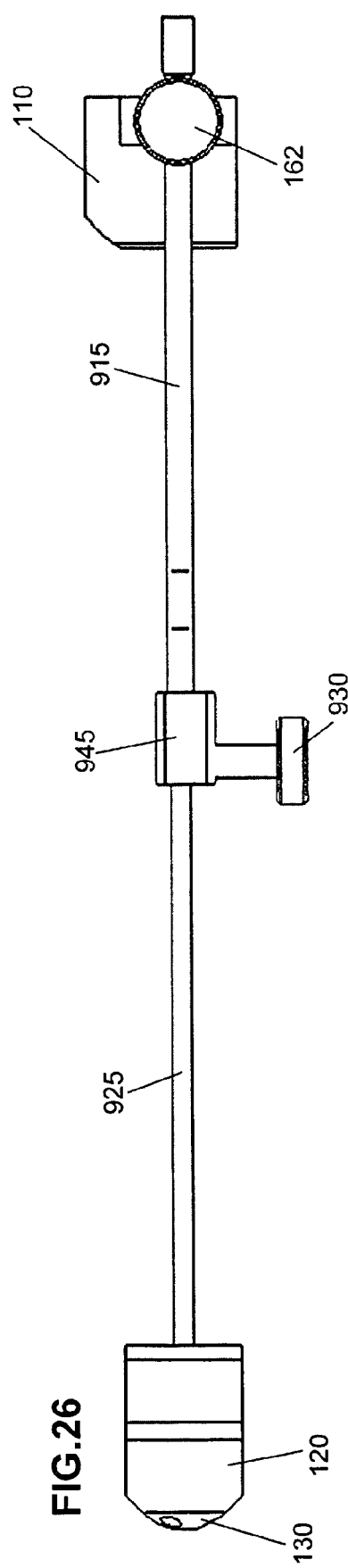
FIG. 26 is a side view of the system of FIG. 25.

Referring now to FIG. 24, another embodiment for a stabilizing plate 120''' is shown. Plate 120''' is similar to plate 120'' described above, except that plate 120''' includes six sets of apertures 915 in addition to the central aperture through which needles from one or more probes can be extended. In this configuration, additional coverage is provided surrounding the target site. In other embodiments, more or fewer sets of apertures can be provided. In yet other embodiments, one or more coils (e.g., coil 310), can be included adjacent each set of apertures 915 of plate 120''' for enhanced tracking, as described below.

Figure 27:
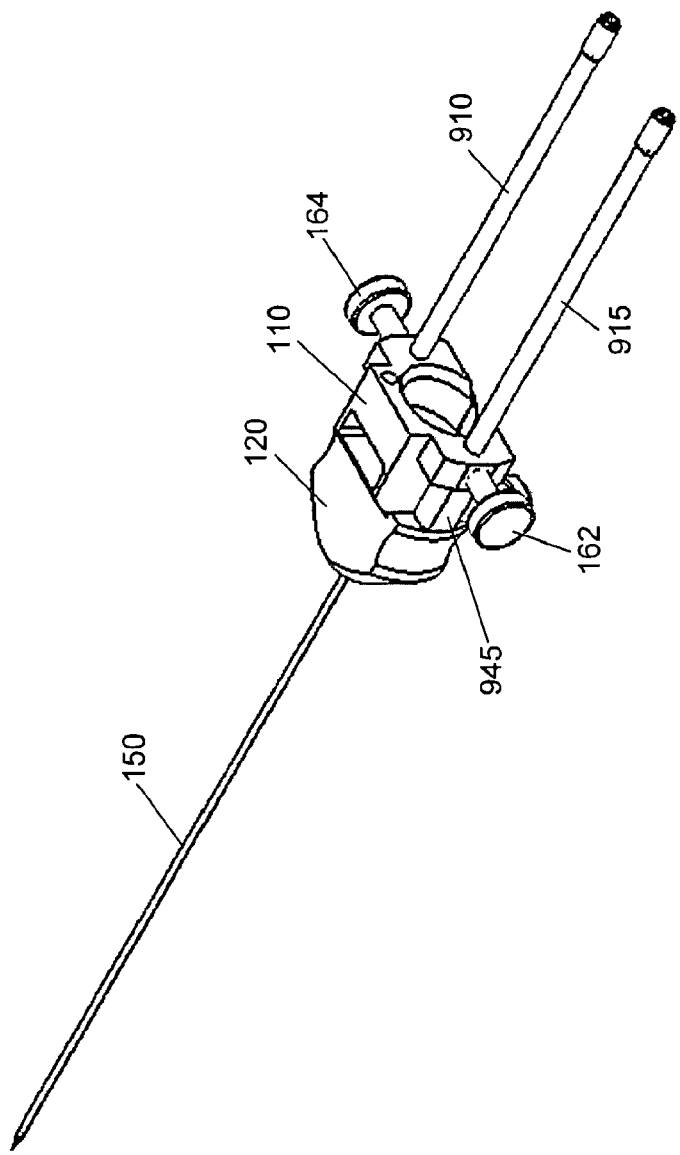
FIG. 27 is another perspective view of the system of FIG. 25.
Figure 28:
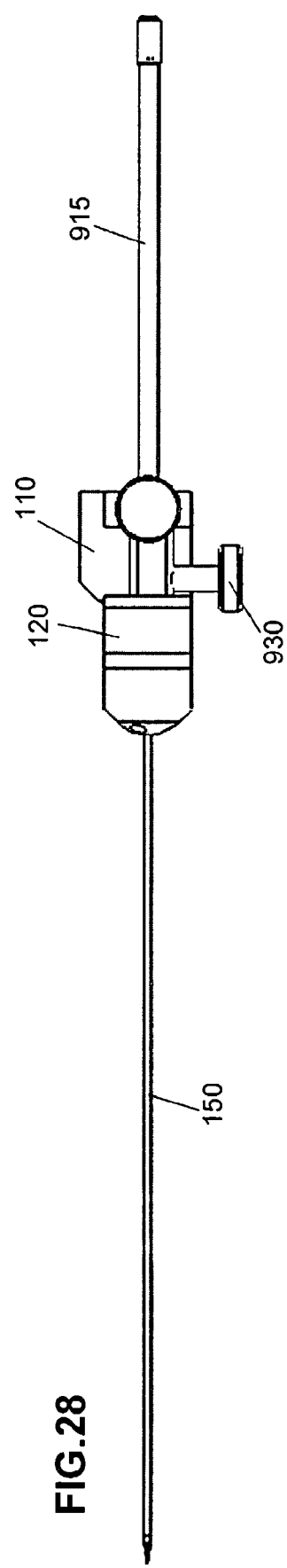
FIG. 28 is a side view of the system of FIG. 27.

Referring now to FIGS. 25-28, another example system 900 is shown. System 900 is similar to system 100 described above, except that system 900 includes first rod portions 910, 915 that telescopically engage second portions 920, 925 at junctions 990, 945. For example, in FIGS. 25 and 26, portions 910, 915 are extended with respect to portions 920, 925. In FIGS. 27 and 28, portions 920, 925 have been telescopically received in portions 910, 915 until plate 120 contacts junctions 990, 945. Lock mechanisms 930, 935 allow portions 910, 915 to be locked in relation to portions 920, 925 at various stages.

Figure 29:
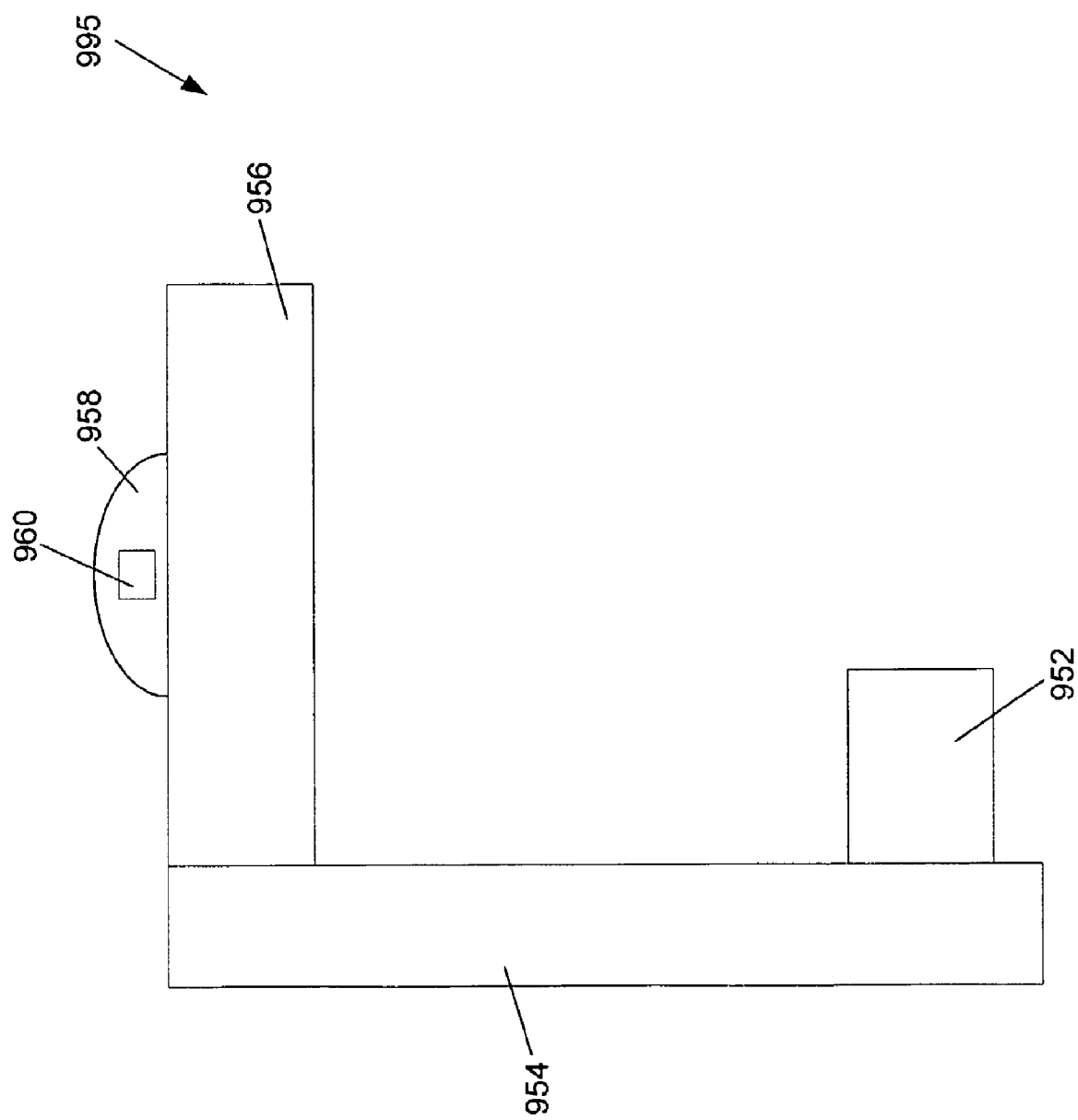
FIG. 29 is a schematic view of another embodiment of an access system made in accordance with principles of the invention.

Referring now to FIG. 29, a schematic view of another embodiment of a system 995 is shown. System 995 includes hub 952, member 954, plate 956, and button 958. In the illustrated example, hub 952 includes a clip that can be used to clip system 995 to a needle or a probe, such as an ultrasound probe (not shown). Once a needle or probe is clipped onto hub 952, hub 952 can be moved along member 954 towards plate 956 to introduce the needle or probe. In addition, in the example shown, button 958 includes a coil 960 that can be tracked to, for example, track positioning of system 995. In the example shown, system 995 can be tracked using coil 958, and a probe can be tracked using a separate coil or another tracking system, such as ultrasound in the case of an ultrasound probe.

Additional details regarding a similar apparatus that can be clipped to a probe such as an ultrasound probe are disclosed in U.S. Pat. No. 5,931,786 to Whitmore III et al. and U.S. patent application Ser. No. 10/636,456 to Barzell et al., the entireties of which are hereby incorporated by reference.

Methods

According to another aspect, the invention relates to a method of providing access to one or more target sites in a body. In some embodiments, methods of accessing one or more target sites can be employed to treat diseased tissue including without limitation tumors, cardiac tissue, sites of abnormal growths and/or bleeding. The treatment can include ablation treatments or delivery of therapeutic agents such as drugs, antibodies, antibody conjugates, and the like. Ablation agents include without limitation radio frequency energy, a cryogenic agent, hot water, ultrasound, and chemotherapy. In addition, other agents such as imaging agents such as radioactive compounds and antibodies conjugated to a detectable label can be delivered. In other embodiments, methods of accessing one or more target sites can be employed to sample or monitor tissues, for example, for diagnostic, prognostic, monitoring of therapeutic efficacy, or for automation of pharmocogenomic tools.

Although some of the examples described herein are described in relation to the delivery of therapy, in other embodiments the systems and methods disclosed herein can be used to perform other functions such as tissue sampling including biopsy. Tissue samples can be used in methods of diagnosis, prognosis, monitoring of therapy, and pharmocogenomics. For example, navigation using the systems and methods disclosed herein can aid in the automation of pharmacogenomic tools. As therapies are individualized in the age of personalized medicine, patient-specific drug cocktails can be chosen based upon the specific genomic profile of a tumor at one time. Individualized therapies will increase efficacy and decrease toxicity. Tumor biopsy can extract mRNA, which can be amplified and studied with cDNA microarray technologies. Specific genes expressed may predict response, toxicity, or the timing of susceptibility to radiation or a specific chemotherapy cocktail. By allowing repeated biopsies over time from the same portion of a tumor, robotics and image registration may normalize and decipher the spatial heterogeneity inherent to tumors, such that reliable genetic and proteomic signatures may be extracted. Using such tools may give the oncologist a clearer window into the changing face of an evolving organism such as a tumor. It will also allow use of functional or metabolic imaging (e.g., PET, MRI, contrast agents) use during biopsy for more accurate tissue acquisition, more accurate tissue characterization, and more accurate information on prognosis, tumor sensitivity to specific drugs, or tumor response to specific drugs.

In one embodiment, the method can include: positioning a member including a semispherical surface against the body; sliding a hub relative to a stabilizing plate to introduce one or more needles or probes into the body; magnetically tracking the needle or probe as it moves through the body; locking the hub relative to the stabilizing plate when the needle or probe reaches the target site; and introducing an ablation agent to the target site through the needle or probe or sampling one or more tissues at the target site. The method may further comprise analyzing the tissue sample for the presence or absence of a diagnostic or prognostic marker, sensitivity to specific drugs, or response to specific drugs, monitoring the efficacy of therapy, analyzing the tissues for gene expression or gene expression profiles.

In some embodiments, methods for using systems 100, 600, 700, 800, 900, and 995 generally include the following. Initially, three-dimensional preoperative imaging of the target area is conducted using, for example, CT imaging or rotational angiography. Next, the three-dimensional image is overlaid on a magnetically trackable space such as that provided by an electromagnetic tracking system such as the AURORA™ system manufactured by Northern Digital Inc. of Ontario, Canada.

Next, needle 140 including coil 310 can be inserted into the body and tracked magnetically using imaged target area that has been overlaid on the magnetically tracked space. Once the target has been reached, probe 410 can be inserted and an ablation agent such as ablation energy can be delivered to the target site using needle 140 and/or one or more needles of probe 410. If multiple sets of apertures are provided (see systems 600, 700, and 800), the same probe or an additional probe 410 can be inserted into one or more of the additional sets of apertures to ablate tissue surrounding the target site.

Additional details regarding methods of using magnetically tracked ablation devices can be found in U.S. patent application Ser. No. 10/377,528, Publication No. 2003/0220557 A1, filed on Feb. 28, 2003, and entitled "Image Guided Liver Interventions Based on Magnetic Tracking of Internal Organ Motion," the entirety of which is hereby incorporated by reference.

Example

Clinical trials utilizing one or more of the systems and methods disclosed herein included Electromagnetic (EM) needle tracking performed during CT guided biopsy and RFA with internal EM sensors integrated into custom needles and tracked RFA guiding buttons (Traxtal Inc.). Pre-procedural CT images were registered to the patient with 6 to 8 skin fiducials. Seventeen procedures (i.e., biopsy or RF ablation) were performed. Example diagnoses included ocular melanoma, breast cancer, hepatitis, VHL, ovarian cancer, HIV, CGD, follicular lymphoma, adrenal cell CA, and RCCA. Procedure sites included liver dome, exophytic kidney tumor, periportal liver, kidney, left lung, and clandestine lesion.

Each needle manipulation that has a CT scan showing needle location served as a gold standard for comparison with the needle position predicted by the tracking system (NDI). Additional tracking data on overall patient motion and breathing was obtained from one to three 6 DoF superficial sensors attached to the sternum and abdomen of the patient. Tracking accuracy, defined as distance between actual CT position of the needle tip and corresponding displayed or "virtual" needle position from the tracking system, was measured. In addition, the scan-to-scan motion of the patient was quantified based on the skin fiducials, and respiratory-induced motion of the tracked needle and skin sensors was measured.

An analysis of ten patients showed a skin fiducial-based registration error ranging from 0.8 mm to 2.7 mm rms. The tracking accuracy at the target position ranged from 2.4 to 8.6 mm rms. The error is incurred in part by respiratory motion of the sedated patients ranging from 7.8 to 12.4 mm (inhale-exhale), and mean scan-to-scan patient motion from 1.4 to 4.4 mm.

EM needle tracking utilizing one or more of the systems disclosed herein can provide valuable guidance during biopsies and ablations and has the potential to significantly improve accuracy and reduce procedure time. EM sensors can be used to track and partly correct for overall patient motion and respiratory motion, and may be useful during repositioning of probes, when imaging feedback can be suboptimal.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. An access system for a device, comprising:
    a plate member defining at least a first aperture, the plate member including a first side and a second side, wherein the first side includes a semispherical surface that is configured to be positioned against a skin surface of a patient;
    a hub defining at least a second aperture and being slideably coupled to the second side of the plate member by a guide passing through the second aperture of the hub;
    a lock mechanism configured to lock the hub relative to the plate member on the guide;
    a removable probe that is inserted through the hub and the plate member; and
    a magnetically trackable sensor;
    wherein, when the semispherical surface is positioned against the skin surface of the patient, the hub is operable to be slid relative to the plate member along the guide until the sensor indicates that the probe is positioned at a target site within the patient.

2. The system of claim 1, wherein the sensor is coupled to one of the hub, a needle coupled to the hub, or the probe.

3. The system of claim 1, wherein the probe includes a stop that limits a distance that the probe can be inserted through the hub.

4. The system of claim 3, wherein the stop is formed by increasing a diameter of the probe such that, when the increased diameter is positioned adjacent to the second aperture of the hub, the probe cannot be inserted further through the second aperture of the hub.

5. The system of claim 1, wherein the probe is one of a single or multi-lumen probe.

6. The system of claim 1, wherein the probe is one of a radio frequency ablation probe, a microwave probe, a biopsy needle, a brachytherapy needle, a cryogenic probe, an ultrasound probe, an optical coherence tomography probe, a laser probe, an electrode, or a hollow cannula.

7. The system of claim 1, wherein the plate member is pivotable about the skin surface using the semispherical surface.

8. The system of claim 1, wherein the guide includes at least one rod.

9. An access system for an ablation device, comprising:
    a plate defining at least a first aperture;
    a member coupled to the plate and defining a semispherical surface configured to be positioned against a skin surface of a patient;
    a hub slideably coupled to the plate by a rod passing through the hub aperture of the hub;
    a lock mechanism configured to lock the hub on the rod relative to the plate; and
    a needle coupled to the hub, the needle including a magnetically trackable coil positioned in a tip of the needle;
    wherein, upon the semispherical surface of the member being positioned against the skin surface of the patient, the hub is slid relative to the plate along the rod to insert the needle through the first aperture of the plate into the skin surface of the patient until the tip reaches a target site, wherein the hub is locked by the lock mechanism when the tip of the needle reaches the target site, and wherein an ablation agent is delivered to the target site through the needle, or a tissue sample is obtained.

10. The system of claim 9, wherein the hub and the plate each define a set of additional apertures, wherein a probe including a plurality of needles is inserted through at least some of the additional apertures of the hub and plate to positions adjacent the target site, and wherein the ablation agent is delivered to the positions adjacent the target site using one or more of the plurality of needles of the probe.

11. The system of claim 9, wherein the plate and the hub each comprises a plurality of sets of additional apertures.

12. The system of claim 9, further comprising a cannula surrounding the needle, wherein the needle is removed upon reaching the target site and a needle of a probe is inserted through the cannula to the target site to deliver the ablation agent to the target site.

13. A method of utilizing an access device to provide access to a target site in a body, the access device including a stabilizing plate having at least a first aperture therethrough, the stabilizing plate including a button having a semispherical surface, the access device further including a needle coupled to a hub, the needle including a trackable sensor at its tip and the hub being slideably connected to the stabilizing plate by a guide passing through a hub aperture of the hub, and the access system further including a lock mechanism configured to lock the hub on the guide relative to the stabilizing plate, the method comprising the acts of:
 positioning the semispherical surface of the button against the body;
 sliding the hub, along the guide that passes through the hub aperture, relative to the stabilizing plate to move the needle through the first aperture of the stabilizing plate, thereby introducing the needle into the body;
 magnetically tracking the tip of the needle as it moves through the body using the trackable sensor;
 locking the hub on the guide relative to the stabilizing plate when the needle reaches the target site; and
 introducing an ablation agent to the target site through the needle, or obtaining a tissue sample at the target site.

14. The method of claim 13, further comprising the act of introducing a probe including a plurality of needles through a plurality of additional apertures in the hub and stabilizing plate, thereby introducing the plurality of needles into the body adjacent to the target site.

15. The method of claim 13, further comprising the acts of:
 imaging an area surrounding the target site in three dimensions to obtain one or more images;
 overlaying the one or more images onto a magnetically tracked spade; and
 using the one or more images overlaid on the magnetically tracked space to track the tip of the needle as the needle is introduced into the body towards the target site.

16. The method of claim 13, wherein the act of positioning the semispherical surface of the button against the surface further comprises the act of rotating or pivoting the semispherical surface of the button against the body to a desired position.

17. The method of claim 13, further comprising the acts of:
 removing the needle upon reaching the target site, wherein a cannula surrounding the needle is left in place; and
 inserting a probe through the cannula to the target site to deliver the ablation agent to the target site.

18. The method of claim 13, wherein the needle is a single or multi-lumen probe.

19. The method of claim 13, wherein the needle is one of a radio frequency ablation probe, a microwave probe, a biopsy needle, a brachytherapy needle, a cryogenic probe, an ultrasound probe, an optical coherence tomography probe, a laser probe, an electrode, or a hollow cannula.

20. The method of claim 13, wherein the needle is a single or multi-lumen radio frequency ablation probe.

21. The access system of claim 1, wherein the guide is fixedly attached to the plate member.

22. The access system of claim 1, further comprising a further guide, wherein the guide and the further guide are fixedly attached to the plate member and are inserted into the second aperture and a third aperture of the hub, respectively, for slideable movement of the hub along the guide and the further guide.

23. The access system of claim 1, wherein the hub further comprises a retainer member having a locked position to retain the hub at a desired position relative to plate member on guide.

* * * * *